US010500255B2

(12) United States Patent
Leren et al.

(10) Patent No.: US 10,500,255 B2
(45) Date of Patent: Dec. 10, 2019

(54) COSMETIC COMPOSITIONS FROM FISH HATCHING FLUID

(71) Applicant: Aqua Bio Technology ASA, Bergen (NO)

(72) Inventors: Hans Kristian Leren, Bergen (NO); Fanny Fagot, Oslo (NO)

(73) Assignee: Aqua Bio Technology ASA, Fornebu (NO)

( * ) Notice: Subject to any disclaimer, the term of this patent is extended or adjusted under 35 U.S.C. 154(b) by 896 days.

(21) Appl. No.: 14/654,146

(22) PCT Filed: Dec. 21, 2012

(86) PCT No.: PCT/EP2012/076853
§ 371 (c)(1),
(2) Date: Jun. 19, 2015

(87) PCT Pub. No.: WO2014/094918
PCT Pub. Date: Jun. 26, 2014

(65) Prior Publication Data
US 2015/0328290 A1    Nov. 19, 2015

(51) Int. Cl.
A61K 38/48    (2006.01)
A61K 38/17    (2006.01)
A61K 8/66    (2006.01)
A61K 8/64    (2006.01)
A61Q 19/00    (2006.01)
A61Q 19/10    (2006.01)
A61K 35/60    (2006.01)
A61K 8/98    (2006.01)

(52) U.S. Cl.
CPC .............. *A61K 38/482* (2013.01); *A61K 8/64* (2013.01); *A61K 8/66* (2013.01); *A61K 8/987* (2013.01); *A61K 35/60* (2013.01); *A61K 38/1706* (2013.01); *A61K 38/4806* (2013.01); *A61Q 19/00* (2013.01); *A61Q 19/007* (2013.01); *A61Q 19/10* (2013.01); *A61K 2800/28* (2013.01)

(58) Field of Classification Search
None
See application file for complete search history.

(56) References Cited

U.S. PATENT DOCUMENTS

| 4,268,499 A | 5/1981 | Keil |
| 2008/0038300 A1 | 2/2008 | Jaspers et al. |
| 2009/0043236 A1 | 2/2009 | Kawamura et al. |

FOREIGN PATENT DOCUMENTS

| WO | 99/29836 | 6/1999 |
| WO | 05/67499 A2 | 7/2005 |
| WO | 2008/020329 | 2/2008 |
| WO | 09/85302 A2 | 7/2009 |
| WO | 2011/064384 | 6/2011 |

OTHER PUBLICATIONS

Decision on granting a patent for invention dated Oct. 25, 2016 in corresponding Russian Application No. 2015127472/15(042703).
Dermaclarine: A natural and gentle skin clarifier, Aqua Bio Technology ASA, Sep. 10, 2012.
International Search Report for PCT/EP2012/076853, dated Mar. 19, 2013.
Offer for Sale of claimed subject matter on Oct. 12, 2012, between parties in Norway.
Offer for Sale of claimed subject matter on Oct. 12, 2012, in the United States.
Oppen-Berntsen et al., The Effects of Hypoxia, Alkalinity and Neurochemicals on Hatching of Atlantic Salmon (*Salmo salar*) Eggs. Aquaculture 86:417-480 (1990).

*Primary Examiner* — David J Blanchard
*Assistant Examiner* — Sarah J Chickos
(74) *Attorney, Agent, or Firm* — Wenderoth, Lind & Ponack, L.L.P.

(57) ABSTRACT

The present invention relates to pharmaceutical or cosmetic compositions obtained or obtainable from fish hatching fluid comprising polypeptides or portions thereof and the use of said compositions in various medical and cosmetic applications to the skin, particularly for moisturizing skin and/or for exfoliation of the horny layer of the skin for treating or preventing skin disorders or conditions in an animal.

12 Claims, 7 Drawing Sheets
Specification includes a Sequence Listing.

A

B

A

B

SEQUENCE LISTING

<160> NUMBER OF SEQ ID NOS: 12

<210> SEQ ID NO 1
<211> LENGTH: 261
<212> TYPE: PRT
<213> ORGANISM: Salmo salar

<400> SEQUENCE: 1

Met Asp His Arg Pro Thr Leu Ser Leu Leu Leu Leu Leu Leu Leu Leu
1               5                   10                  15

Gly Leu Ser Gln Ala Ser Gly Asn Glu Phe His Asp Glu Pro Asp His
            20                  25                  30

Val Ser Ile Thr Ser Val Ile Leu Lys Ser Asn Asn Gly Thr Asn Glu
        35                  40                  45

Leu Leu Leu Asp Gly Asp Ile Leu Ala Pro Arg Thr Arg Asn Ala Met
    50                  55                  60

Lys Cys Phe Ser Ser Gln Tyr Ser Cys Leu Trp Lys Lys Ser Ser Asp
65                  70                  75                  80

Gly Leu Val Tyr Val Pro Tyr Ile Leu Ser Ala Val Tyr Ser Ser Leu
                85                  90                  95

Glu Val Glu Thr Ile Glu Thr Ala Met Lys Tyr Phe Gln Gly Lys Thr
            100                 105                 110

Cys Ile Arg Phe Ile Pro Arg Lys Thr Gln Thr Ala Tyr Leu Asp Ile
        115                 120                 125

Gln Ser Ser Gly Gly Cys Phe Gly Thr Val Gly Thr Val Gly Asp Arg
    130                 135                 140

Gln Thr Leu Ser Leu Ala Gln Phe Gly Cys Val Gln His Gly Ile Ile
145                 150                 155                 160

Gln His Glu Leu Leu His Ala Leu Gly Phe His Glu His Asn Arg Ser
                165                 170                 175

Asp Arg Glu Gln Tyr Ile Arg Ile Asn Trp Gln Tyr Ile Tyr Asp Tyr
            180                 185                 190

Ala Val Gly Asn Phe Gln Lys Glu Asp Thr Asn Asn Leu His Thr Ala
        195                 200                 205

Tyr Asp Tyr Ser Ser Val Met His Tyr Asp Arg Thr Ala Tyr Thr Asn
    210                 215                 220

Asp Tyr Gly Lys Glu Thr Ile Thr Pro Ile Pro Asp Pro Ser Val Ala
225                 230                 235                 240

Ile Gly Gln Arg Leu Gly Met Ser Asp Ile Asp Val Leu Lys Val Asn
                245                 250                 255

Lys Leu Tyr Gln Cys
            260

<210> SEQ ID NO 2
<211> LENGTH: 117
<212> TYPE: PRT
<213> ORGANISM: Salmo salar

<400> SEQUENCE: 2

```
Thr Val Thr Val Gln Cys Thr Lys Asp Gly Gln Phe Val Val Val
1               5                   10                  15

Ser Arg Asp Ala Thr Leu Pro Asn Leu Glu Leu Asp Ser Ile Ser Leu
                20                  25                  30

Leu Gly Ala Asn Gly Ala His Cys Thr Pro Val Gly Thr Thr Ser Ala
            35                  40                  45

Phe Ala Ile Tyr Gln Phe Lys Val Thr Glu Cys Gly Thr Val Val Thr
        50                  55                  60

Glu Glu Pro Asp Thr Ile Val Tyr Glu Asn Arg Met Ser Ser Ser Tyr
65                  70                  75                  80

Val Val Gly Ile Gly Pro Phe Gly Asp Ile Thr Arg Asp Ser His Tyr
                85                  90                  95

Asp Leu Val Phe Gln Cys Arg Tyr Thr Gly Thr Ser Val Glu Thr Leu
            100                 105                 110

Val Ile Glu Val Lys
            115
```

<210> SEQ ID NO 3
<211> LENGTH: 261
<212> TYPE: PRT
<213> ORGANISM: Salmo salar

<400> SEQUENCE: 3

```
Ala Val Thr Val Gln Cys Thr Lys Asp Gly Gln Phe Val Val Val
1               5                   10                  15

Ala Arg Asp Ala Thr Leu Pro Ser Leu Glu Leu Asp Ser Ile Ser Leu
                20                  25                  30

Leu Gly Thr Asn Gly Pro His Cys His Ala Ile Gly Thr Thr Ser Val
            35                  40                  45

Phe Ala Ile Tyr Gln Phe Lys Val Thr Glu Cys Gly Thr Val Met Thr
        50                  55                  60

Glu Glu Thr Asp Thr Ile Ile Tyr Glu Asn Arg Met Ser Ser Ser Tyr
65                  70                  75                  80

Gln Val Gly Val Gly Pro Phe Gly Ser Ile Thr Arg Asp Ser Gln Tyr
                85                  90                  95

Asp Leu Thr Phe Gln Cys Arg Tyr Lys Gly Ser Thr Ile Val Ala Val
            100                 105                 110

Val Ile Asp Val Lys Pro Val Pro Pro Asn Pro Asp Ile Ala Pro
            115                 120                 125

Gly Pro Leu Thr Val Glu Leu Arg Leu Gly Ser Gly Thr Cys Leu Thr
        130                 135                 140

Lys Gly Cys Asn Glu Glu Glu Val Ala Tyr Thr Ser Tyr Tyr Thr Glu
145                 150                 155                 160

Ala Asp Tyr Pro Val Thr Lys Val Leu Arg Asp Pro Val Tyr Thr Glu
                165                 170                 175

Val Arg Ile Leu Ala Arg Thr Asp Pro Asn Ile Val Leu Thr Leu Gly
            180                 185                 190

Arg Cys Trp Ala Thr Thr Asn Pro Asn Pro Leu Ser Leu Pro Gln Trp
        195                 200                 205

Asp Leu Leu Ile Asp Gly Cys Pro Tyr Gln Asp Asp Arg Tyr Leu Thr
    210                 215                 220

Thr Pro Ile Asn Val Gly Pro Ser Ser Gly Leu Ser Phe Pro Thr His
225                 230                 235                 240
```

-continued

```
Tyr Arg Arg Phe Val Leu Lys Met Phe Thr Phe Val Asp Pro Met Ser
            245                 250                 255
Met Thr Pro Leu Arg
            260

<210> SEQ ID NO 4
<211> LENGTH: 224
<212> TYPE: PRT
<213> ORGANISM: Salmo salar

<400> SEQUENCE: 4

Ala Glu Cys Arg Glu Asn Met Val His Val Glu Ala Lys His Asp Leu
1               5                   10                  15
Leu Gly Ile Gly Gln Leu Ile Gln Leu Glu Asp Leu Thr Leu Gly Asp
                20                  25                  30
Cys Pro Met Ser Gly Phe Asp Asn Ile Asn Gln Val Leu Ile Phe Glu
            35                  40                  45
Ser Pro Leu Gln Ser Cys Gly Ser Gln Leu Arg Met Thr Thr Asn Ser
        50                  55                  60
Leu Ile Tyr Ile Phe Thr Leu Tyr Tyr Lys Pro Lys Pro Leu Ala Asn
65                  70                  75                  80
Thr Pro Leu Ile Arg Thr Asn Asp Ala Met Ile Asn Ile Glu Cys His
                85                  90                  95
Tyr Pro Arg Lys His Asn Val Ser Ser Leu Ala Leu Ile Pro Thr Trp
            100                 105                 110
Thr Pro Phe Ser Ala Ala Lys Tyr Ala Glu Glu Leu Leu Tyr Phe Ser
        115                 120                 125
Met Arg Leu Met Thr Ala Asp Trp Gln Tyr Glu Arg Ala Gly Asn Met
130                 135                 140
Tyr Val Leu Gly Asp Met Val Asn Ile Glu Ala Ser Val Met Gln Tyr
145                 150                 155                 160
Phe His Val Pro Leu Arg Ile Phe Val Asp Ser Cys Val Ala Thr Leu
                165                 170                 175
Glu Pro Asn Ile Asn Ala Asn Pro Arg Tyr Ala Phe Ile Glu Asn His
            180                 185                 190
Gly Cys Leu Ile Asp Ala Lys Met Thr Gly Ser His Ser Gln Phe Met
        195                 200                 205
Pro Arg Ser Ala Asp Tyr Lys Leu Tyr Phe Gln Val Glu Ala Phe Arg
    210                 215                 220

<210> SEQ ID NO 5
<211> LENGTH: 439
<212> TYPE: PRT
<213> ORGANISM: Salmo salar

<400> SEQUENCE: 5

Met Lys Trp Ser Ala Val Cys Leu Val Ala Val Ala Thr Leu Gly Trp
1               5                   10                  15
Leu Cys Asp Ala Gln Asn Phe Leu Glu Lys Pro Gly Trp Pro Pro Ile
                20                  25                  30
Gln Thr Pro Pro Ser Trp Pro Pro Gln Thr Pro Gln Arg Pro Val Gln
            35                  40                  45
Pro Leu Pro Gln Arg Pro Ala Gln Pro Phe Leu Gln Lys Pro Ala Gln
        50                  55                  60
Pro Ile Pro Gln Arg Ile Pro Tyr Thr Glu Asp Asp Thr Lys Gln Thr
65                  70                  75                  80
```

-continued

```
Cys Glu Val Val Asp Lys Asp Lys Val Ser Cys Gly Leu Ser Gly Ile
             85                  90                  95

Thr Ala Ala Gln Cys Gln Ala Ile Ser Cys Cys Phe Asp Gly Arg Met
            100                 105                 110

Cys Phe Tyr Gly Lys Thr Val Thr Val Gln Cys Thr Lys Asp Gly Gln
            115                 120                 125

Phe Val Val Val Ser Arg Asp Ala Thr Leu Pro Asn Leu Glu Leu
            130                 135             140

Asp Ser Ile Ser Leu Leu Gly Ala Asn Gly Ala His Cys Thr Pro Val
145                 150                 155                 160

Gly Thr Thr Ser Ala Phe Ala Ile Tyr Gln Phe Lys Val Thr Glu Cys
                165                 170                 175

Gly Thr Val Val Thr Glu Glu Pro Asp Thr Ile Val Tyr Glu Asn Arg
            180                 185                 190

Met Ser Ser Ser Tyr Val Val Gly Ile Gly Pro Phe Gly Asp Ile Thr
            195                 200                 205

Arg Asp Ser His Tyr Asp Leu Val Phe Gln Cys Arg Tyr Thr Gly Thr
            210                 215                 220

Ser Val Glu Thr Leu Val Ile Glu Val Lys Thr Tyr Pro Asn Pro Asn
225                 230                 235                 240

Pro Val Val Thr Val Asp Ala Val Leu Asn Val Glu Leu Arg Leu Ala
            245                 250                 255

Asn Gly Arg Cys Leu Ser Lys Gly Cys Asp Glu Met Gln Glu Ala Tyr
            260                 265                 270

Thr Ser Tyr Tyr Thr Val Ala Asp Tyr Pro Val Thr Lys Val Leu Arg
            275                 280                 285

Asp Pro Val Tyr Ala Glu Val Arg Ile Leu Gly Met Thr Asp Pro Asn
            290                 295                 300

Val Val Leu Thr Leu Glu Gln Cys Trp Ala Thr Ile Asp Pro Thr Gly
305                 310                 315                 320

Asp Arg Leu Pro Arg Trp Asp Leu Leu Asn Gly Cys Pro Tyr Gln
            325                 330                 335

Asp Asp Arg Tyr Leu Thr Val Pro Ile Ala Ser Asp Ser Ser Tyr Ile
            340                 345                 350

Pro Pro Gly Glu Phe Leu Ser His Tyr Lys Arg Phe Val Phe Lys Met
            355                 360                 365

Phe Thr Phe Val Asp Pro Thr Ser Met Val Pro Leu Gln Glu Asn Val
            370                 375                 380

Tyr Ile His Cys Arg Ala Thr Val Cys His Ala Leu Ala Gly Ser Cys
385                 390                 395                 400

Glu Gln Arg Cys Asn Arg Gln Arg Asp Leu Ser Ala Gln Gly Gln
            405                 410                 415

Lys Lys Thr Lys Gly Asp Val Val Ser Ser Gln Lys Val Ile Met
            420                 425                 430

Ile Asp Pro Ser Leu Tyr Ala
            435
```

<210> SEQ ID NO 6
<211> LENGTH: 524
<212> TYPE: PRT
<213> ORGANISM: Oncorhynchus masou

<400> SEQUENCE: 6

```
Met Lys Trp Ser Ala Val Cys Leu Val Ala Val Ala Thr Leu Gly Trp
1               5                   10                  15
```

```
Leu Cys Asp Ala Gln Ile Tyr Leu Glu Lys Pro Gly Trp Pro Pro Ile
            20                  25                  30
Gln Thr Pro Ala Ser Trp Pro Ala Gln Pro Pro Glu Lys Pro Val Gln
            35                  40                  45
Pro Pro Gln Arg Pro Ala Gln Pro Pro Gln Trp Pro Ala Gln Pro Pro
 50                  55                  60
Gln Trp Pro Ala Gln Pro Pro Gln Arg Pro Ala Gln Pro Pro Gln Arg
 65                  70                  75                  80
Pro Ala Gln Thr Gln Gln Trp Pro Gly Gln Pro Pro Gln Arg Pro Ala
                85                  90                  95
Gln Pro Pro Gln Trp Pro Ala Gln Pro Gln Arg Pro Ala Gln Pro
            100                 105                 110
Pro Gln Arg Pro Ala Gln Pro Gln Arg Pro Ala Gln Pro Pro
        115                 120                 125
Arg Pro Ala Gln Pro Pro Gln Trp Pro Val His Pro Pro Gln Trp Pro
130                 135                 140
Val Gln Pro Gly Thr Pro Leu Gln Arg Pro Lys Phe Pro Ser Asp Pro
145                 150                 155                 160
Gly Ser Lys Gln Ser Cys Asp Val Asp Ser Gln His Lys Val Gln Cys
                165                 170                 175
Gly Leu Pro Asp Ile Thr Ala Ala His Cys Asp Ala Ile Asn Cys Cys
            180                 185                 190
Phe Asp Gly Arg Met Cys Phe Tyr Gly Lys Ala Val Thr Val Gln Cys
            195                 200                 205
Thr Lys Asp Gly Gln Phe Val Val Val Ala Arg Asp Ala Thr Leu
            210                 215                 220
Pro Ser Leu Glu Leu Asp Ser Ile Ser Leu Leu Gly Thr Asn Gly Pro
225                 230                 235                 240
His Cys His Ala Ile Gly Thr Thr Ser Val Phe Ala Ile Tyr Gln Phe
                245                 250                 255
Lys Val Thr Glu Cys Gly Thr Val Met Thr Glu Thr Asp Thr Ile
            260                 265                 270
Ile Tyr Glu Asn Arg Met Ser Ser Tyr Gln Val Gly Val Gly Pro
            275                 280                 285
Phe Gly Ser Ile Thr Arg Asp Ser Gln Tyr Asp Leu Thr Phe Gln Cys
290                 295                 300
Arg Tyr Lys Gly Ser Thr Ile Val Ala Val Ile Asp Val Lys Pro
305                 310                 315                 320
Val Pro Pro Asn Pro Asp Ile Ala Pro Gly Leu Thr Val Glu
            325                 330                 335
Leu Arg Leu Gly Ser Gly Thr Cys Leu Thr Lys Gly Cys Asn Glu Glu
            340                 345                 350
Glu Val Ala Tyr Thr Ser Tyr Tyr Thr Glu Ala Asp Tyr Pro Val Thr
            355                 360                 365
Lys Val Leu Arg Asp Pro Val Tyr Thr Glu Val Arg Ile Leu Ala Arg
            370                 375                 380
Thr Asp Pro Asn Ile Val Leu Thr Leu Gly Arg Cys Trp Ala Thr Thr
385                 390                 395                 400
Asn Pro Asn Pro Leu Ser Leu Pro Gln Trp Asp Leu Leu Ile Asp Gly
            405                 410                 415
Cys Pro Tyr Gln Asp Asp Arg Tyr Leu Thr Thr Pro Ile Asn Val Gly
            420                 425                 430
```

```
Pro Ser Ser Gly Leu Ser Phe Pro Thr His Tyr Arg Arg Phe Val Leu
        435                 440                 445

Lys Met Phe Thr Phe Val Asp Pro Met Ser Met Thr Pro Leu Arg Glu
450                     455                 460

Thr Val Phe Ile His Cys Asn Thr Ala Val Cys Leu Pro Ser His Gly
465                 470                 475                 480

Asp Ser Cys Glu Pro Arg Cys Tyr Arg Lys Arg Asp Ile Pro Ala
                485             490             495

Ala Val Gln Lys Thr Thr Arg Ile Lys Ser Asn Leu Val Ser Ser Gly
            500                 505                 510

Glu Leu Ile Leu Thr Asp Pro Arg Glu Leu Thr Asn
        515                 520
```

<210> SEQ ID NO 7
<211> LENGTH: 438
<212> TYPE: PRT
<213> ORGANISM: Oncorhynchus masou

<400> SEQUENCE: 7

```
Met Ala Met Lys Trp Ser Val Val Cys Leu Val Ala Val Ala Met Leu
1               5                   10                  15

Gly Cys Leu Cys Val Ala Gln Ile Trp Pro Ser Ile Lys Pro Val
            20                  25                  30

Gln Gln Pro Phe Arg Pro Asn Arg Pro Pro Gln Gln Pro Gln Gln
            35                  40                  45

Pro Pro Tyr Gln Lys Pro Arg Ile Pro Pro Lys Asp Gln Thr Gln Ala
    50                  55                  60

Lys Gln Lys Phe Glu Thr Pro Leu Asp Trp Thr Tyr Pro Leu Asp Pro
65                  70                  75                  80

Lys Pro Glu Pro Lys Ile Ile Gly Gly Ser Glu Ala Arg Thr Pro Val
                85                  90                  95

Ala Ala Asn Ser Val Arg Ala Glu Cys Arg Glu Asn Met Val His Val
            100                 105                 110

Glu Ala Lys His Asp Leu Leu Gly Ile Gly Gln Leu Ile Gln Leu Glu
            115                 120                 125

Asp Leu Thr Leu Gly Asp Cys Pro Met Ser Gly Phe Asp Asn Ile Asn
130                 135                 140

Gln Val Leu Ile Phe Glu Ser Pro Leu Gln Ser Cys Gly Ser Gln Leu
145                 150                 155                 160

Arg Met Thr Thr Asn Ser Leu Ile Tyr Ile Phe Thr Leu Tyr Tyr Lys
                165                 170                 175

Pro Lys Pro Leu Ala Asn Thr Pro Leu Ile Arg Thr Asn Asp Ala Met
            180                 185                 190

Ile Asn Ile Glu Cys His Tyr Pro Arg Lys His Asn Val Ser Ser Leu
            195                 200                 205

Ala Leu Ile Pro Thr Trp Thr Pro Phe Ser Ala Ala Lys Tyr Ala Glu
    210                 215                 220

Glu Leu Leu Tyr Phe Ser Met Arg Leu Met Thr Ala Asp Trp Gln Tyr
225                 230                 235                 240

Glu Arg Ala Gly Asn Met Tyr Val Leu Gly Asp Met Asn Ile Glu
                245                 250                 255

Ala Ser Val Met Gln Tyr Phe His Val Pro Leu Arg Ile Phe Val Asp
            260                 265                 270

Ser Cys Val Ala Thr Leu Glu Pro Asn Ile Asn Ala Asn Pro Arg Tyr
275                 280                 285
```

```
Ala Phe Ile Glu Asn His Gly Cys Leu Ile Asp Ala Lys Met Thr Gly
            290                 295                 300

Ser His Ser Gln Phe Met Pro Arg Ser Ala Asp Tyr Lys Leu Tyr Phe
305                 310                 315                 320

Gln Val Glu Ala Phe Arg Phe Gln Ser Gln Arg Gly Ser Asp Pro Ile
                325                 330                 335

Ile Pro Gln Lys Thr Lys Ile Pro Phe Gln Pro Ala Ala Asp Tyr Pro
                340                 345                 350

Ala Thr Leu Asp Met Ile Phe Leu Thr Cys His Leu Lys Ala Thr Thr
            355                 360                 365

Ile Ala Phe Pro Ile Asp Phe Glu Tyr Lys Ala Cys Ser Phe Ile Asn
            370                 375                 380

Thr Trp Arg Glu Ala Gly Gly Asn Asp Gly Val Cys Gly Cys Cys Asp
385                 390                 395                 400

Ser Thr Cys Ser Asn Arg Lys Gly Arg Asp Thr Thr Thr His Gln Lys
                405                 410                 415

Pro Ala Asn Ile Trp Glu Gly Asp Val Gln Leu Gly Pro Ile Phe Ile
                420                 425                 430

Ser Glu Lys Val Glu Gln
            435

<210> SEQ ID NO 8
<211> LENGTH: 467
<212> TYPE: PRT
<213> ORGANISM: Salmo salar

<400> SEQUENCE: 8

Lys Trp Ser Tyr Gln Leu Pro Gln Lys Leu Ala Gln Pro Leu Pro Gln
1               5                   10                  15

Lys Pro Ala Gln Pro Leu Pro Gln Trp Pro Val Gln Pro Leu Pro Gln
                20                  25                  30

Arg Pro Ala Glu Pro Leu Pro Gln Arg Pro Ala Gln Pro Leu Pro Gln
            35                  40                  45

Trp Pro Val Gln Pro Leu Pro Gln Arg Pro Ala Glu Pro Leu Pro Gln
50                  55                  60

Arg Pro Ala Gln Pro Leu Pro Gln Arg Pro Val Gln Pro Leu Pro Gln
65                  70                  75                  80

Arg Pro Ala Gln Pro Phe Leu Gln Lys Pro Ala Gln Pro Ile Pro Gln
                85                  90                  95

Arg Ile Pro Tyr Thr Lys Asp Asp Thr Lys Gln Thr Cys Glu Val Val
                100                 105                 110

Asp Lys Asp Lys Val Ser Cys Gly Leu Ser Gly Ile Thr Ala Ala Gln
            115                 120                 125

Cys Gln Ala Ile Ser Cys Cys Phe Asp Gly Arg Met Cys Phe Tyr Gly
            130                 135                 140

Lys Thr Val Thr Phe Gln Cys Thr Lys Asp Gly Gln Phe Val Val Val
145                 150                 155                 160

Val Ser Arg Asp Ala Thr Leu Pro Asn Leu Glu Leu Asp Ser Ile Ser
                165                 170                 175

Leu Leu Gly Ala Asn Gly Ala His Cys Thr Pro Val Gly Thr Thr Ser
            180                 185                 190

Ala Phe Ala Ile Tyr Gln Phe Lys Val Thr Glu Cys Gly Thr Val Val
            195                 200                 205

Thr Glu Glu Pro Asp Thr Ile Val Tyr Glu Asn Arg Met Ser Ser Ser
```

```
                    210                 215                 220
Tyr Val Val Gly Ile Gly Pro Phe Gly Asp Ile Thr Arg Asp Ser His
225                 230                 235                 240

Tyr Asp Leu Val Phe Gln Cys Arg Tyr Thr Gly Thr Ser Val Glu Thr
                245                 250                 255

Leu Val Ile Glu Val Lys Thr Tyr Pro Asn Pro Asn Pro Val Val Thr
            260                 265                 270

Val Asp Ala Val Leu Asn Val Glu Leu Arg Leu Ala Asn Gly Arg Cys
        275                 280                 285

Leu Ser Lys Gly Cys Asp Glu Met Gln Glu Ala Tyr Thr Ser Tyr Tyr
    290                 295                 300

Thr Val Ala Asp Tyr Pro Val Thr Lys Val Leu Arg Asp Pro Val Tyr
305                 310                 315                 320

Ala Glu Val Arg Ile Leu Gly Met Thr Asp Pro Asn Val Val Leu Thr
                325                 330                 335

Leu Glu Gln Cys Trp Ala Thr Thr Asp Pro Thr Gly Asp Arg Leu Pro
            340                 345                 350

Arg Trp Asp Leu Leu Val Asn Gly Cys Pro Tyr Gln Asp Asp Arg Tyr
        355                 360                 365

Leu Thr Val Pro Ile Ala Ser Asp Ser Ser Tyr Ile Pro Pro Gly Glu
    370                 375                 380

Phe Leu Ser His Tyr Lys Arg Phe Val Phe Lys Met Phe Thr Phe Val
385                 390                 395                 400

Asp Pro Thr Ser Met Val Pro Leu Gln Glu Asn Val Tyr Ile His Cys
                405                 410                 415

Arg Ala Thr Val Cys His Ala Leu Ala Gly Ser Cys Glu Gln Arg Cys
            420                 425                 430

Asn Arg Gln Arg Arg Asp Leu Ser Ala Gln Gly Gln Lys Lys Thr Lys
        435                 440                 445

Gly Asp Val Val Ser Ser Gln Lys Val Ile Met Ile Asp Pro Ser
    450                 455                 460

Leu Tyr Ala
465

<210> SEQ ID NO 9
<211> LENGTH: 255
<212> TYPE: PRT
<213> ORGANISM: Salmo salar

<400> SEQUENCE: 9

Met Arg Thr Thr Ala Ala Phe Leu Leu Val Leu Cys Leu Leu Ala Ile
1               5                   10                  15

Ser His Ala Trp Asp Cys Gln Glu Val Val Asn Ile Lys Asn Leu Met
                20                  25                  30

Gln Ile Asp Ala Gly Leu Gly Gln Val Val Ala Thr Asp Thr Ser Gln
            35                  40                  45

Ile Pro Tyr Tyr Leu Val Gly Asp Lys Trp Ile Arg Leu Pro Gly Ser
        50                  55                  60

Leu Lys His Ile Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                85                  90                  95

Gly Leu Leu Lys Gln Leu Asp Ala Gly Gly Glu Gln Phe Ile Val Gly
            100                 105                 110
```

```
Ala Asn Met Asn Asp Thr Pro Tyr Cys Leu Thr Ser Ser Ala Thr Val
                115                 120                 125

Gly Tyr Lys Gly Pro Gly Ser Pro Leu Pro Trp Thr Gly Leu Pro Gly
    130                 135                 140

Ala Val Lys Tyr Tyr Ser Cys Gly Pro Phe Gly Cys Trp Ala Val Asn
145                 150                 155                 160

Lys Asn Asp Asp Ile Tyr Leu Met Ser Leu Asn Gln Asp Cys Gln Asn
                165                 170                 175

Lys Gly Trp Ser His Ile Glu Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Ser Lys Ser Ala Val Thr Met Val Cys Thr His
                245                 250                 255

<210> SEQ ID NO 10
<211> LENGTH: 208
<212> TYPE: PRT
<213> ORGANISM: Salmo salar

<400> SEQUENCE: 10

Ser Ile Pro Tyr Tyr Leu Val Gly Asp Lys Trp Ile Arg Leu Pro Gly
1               5                   10                  15

Ser Leu Lys His Ile Thr Val Gly Pro Ala Gly Ile Trp Gly Val Asn
                20                  25                  30

Lys Asp Tyr Ala Ile Tyr Lys Tyr Val Ala Gly Asn Trp Val Gln Ala
            35                  40                  45

Ala Gly Leu Pro Lys Gln Leu Asp Ala Gly Glu Gln Phe Ile Val
        50                  55                  60

Gly Ala Asn Met Asp Asp Thr Pro Tyr Cys Leu Thr Ser Ser Ala Thr
65                  70                  75                  80

Val Gly Tyr Lys Gly Pro Gly Ser Pro Leu Pro Trp Thr Gly Leu Pro
                85                  90                  95

Gly Ala Val Lys Tyr Tyr Ser Cys Gly Pro Phe Gly Cys Trp Ala Val
            100                 105                 110

Asn Lys Asn Asp Asp Ile Tyr Leu Met Ser Leu Asn Gln Asp Cys Gln
        115                 120                 125

Asn Asn Gly Trp Ser His Ile Glu Gly Lys Leu Ser Met Ile Glu Val
    130                 135                 140

Ala Thr Asp Gly Ser Val Phe Gly Val Asn Ser Ala Gly Ser Val Tyr
145                 150                 155                 160

Thr Arg Asp Gly Ile Thr Ala Ser Lys Pro Glu Gly Thr Gly Trp Ser
                165                 170                 175

Asn Ile Pro Met Cys Met Leu Met Gly His Val Thr Tyr Asp Leu Gly
            180                 185                 190

Arg Leu Trp Val Val Ser Lys Ser Ala Val Thr Met Val Cys Thr His
        195                 200                 205

<210> SEQ ID NO 11
<211> LENGTH: 255
<212> TYPE: PRT
<213> ORGANISM: Salmo salar
```

-continued

```
<400> SEQUENCE: 11

Met Arg Thr Thr Ala Ala Phe Leu Leu Val Leu Cys Leu Leu Ala Ile
1               5                   10                  15

Ser His Ala Trp Asp Cys Gln Glu Val Val Asn Ile Lys Asn Leu Met
            20                  25                  30

Gln Ile Asp Ala Gly Leu Gly Gln Val Val Ala Thr Asp Thr Ser Gln
        35                  40                  45

Ile Pro Tyr Tyr Leu Val Gly Asp Lys Trp Ile Arg Leu Pro Gly Ser
    50                  55                  60

Leu Lys His Ile Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                85                  90                  95

Gly Leu Leu Lys Gln Leu Asp Ala Gly Gly Asn Gln Phe Val Val Gly
            100                 105                 110

Ala Asn Met Asp Asp Thr Pro Phe Cys Leu Thr Ser Ser Ala Thr Val
        115                 120                 125

Gly Tyr Lys Gly Pro Gly Ser Pro Leu Pro Trp Thr Gly Leu Pro Gly
    130                 135                 140

Ala Val Lys Tyr Tyr Ser Cys Gly His Phe Gly Cys Trp Ala Val Asn
145                 150                 155                 160

Lys Asn Asp Asp Ile Phe Leu Met Ser Leu Asn Gln Asp Cys Gln Asn
                165                 170                 175

Asn Gly Trp Ser His Ile Asp Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
    210                 215                 220

Ile Pro Met Gly Met Leu Met Gly His Val Thr Tyr Asp Leu Gly Arg
225                 230                 235                 240

Leu Trp Val Val Ser Lys Ser Gly Gly Thr Met Val Cys Thr His
                245                 250                 255

<210> SEQ ID NO 12
<211> LENGTH: 255
<212> TYPE: PRT
<213> ORGANISM: Salmo salar

<400> SEQUENCE: 12

Met Gly Thr Thr Ala Ala Phe Leu Leu Val Leu Cys Leu Leu Ala Ile
1               5                   10                  15

Ser His Ala Trp Asp Cys Gln Glu Val Val Asn Ile Lys Asn Leu Met
            20                  25                  30

Gln Ile Asp Ala Gly Leu Gly Gln Val Val Ala Thr Asp Thr Ser Gln
        35                  40                  45

Ile Pro Tyr Tyr Leu Val Gly Asp Lys Trp Ile Arg Leu Pro Gly Ser
    50                  55                  60

Leu Lys His Ile Thr Val Gly Pro Ala Gly Ile Trp Gly Val Asn Lys
65                  70                  75                  80

Asp Tyr Ala Ile Tyr Lys Tyr Val Ala Gly Asn Trp Val Gln Ala Ala
                85                  90                  95

Gly Leu Leu Lys Gln Leu Asp Ala Gly Gly Glu Gln Phe Ile Val Gly
            100                 105                 110
```

```
Ala Asn Met Asn Asp Thr Pro Tyr Cys Leu Thr Ser Ser Ala Thr Val
        115                 120                 125

Gly Tyr Lys Gly Pro Gly Ser Pro Leu Pro Trp Thr Gly Leu Pro Gly
    130                 135                 140

Ala Val Lys Tyr Ser Cys Gly Pro Phe Gly Cys Trp Ala Val Asn
145             150                 155                 160

Lys Asn Asp Asp Ile Tyr Leu Met Ser Leu Asn Gln Asp Cys Gln Asn
                165                 170                 175

Lys Gly Trp Ser His Ile Glu Gly Lys Leu Ser Met Ile Glu Val Ala
            180                 185                 190

Thr Asp Gly Ser Val Phe Gly Val Asn Ser Ala Gly Ser Val Tyr Thr
        195                 200                 205

Arg Asp Gly Ile Thr Ala Ser Lys Pro Glu Gly Thr Gly Trp Ser Asn
        210                 215                 220

Ile Pro Met Gly Met Leu Met Gly His Val Thr Tyr Asp Leu Gly Arg
225                 230                 235                 240

Leu Trp Val Val Tyr Lys Ser Ala Val Thr Met Val Cys Thr His
                245                 250                 255
```

COSMETIC COMPOSITIONS FROM FISH HATCHING FLUID

The present invention relates to methods for the production of a composition comprising polypeptides and/or portions of polypeptides, which is derivable from fish hatching fluid, and its use in various applications to the skin. In particular, the compositions comprising said polypeptides and/or portions of polypeptides, are useful in treating various medical and cosmetic skin disorders or conditions.

The skin is one of the more vulnerable organs of the body. Though seldom life-threatening, skin disorders or conditions can be uncomfortable and may cause chronic disabilities. In addition, because the skin is so visible, skin disorders and conditions can lead to psychological stress. There is therefore a continuing need for effective treatments of skin conditions and disorders.

Skin forms the largest organ of the body, accounting for about 12-16 percent of a person's weight. It performs many vital roles as both a barrier and a regulating influence between the outside world and the controlled environment within our bodies.

Skin consists of 3 layers, namely the epidermis, dermis and subcutis. The epidermis is the uppermost, epithelial layer of the skin. It acts as a physical barrier, preventing loss of water from the body, and preventing entry of substances and organisms into the body. Its thickness varies according to body site.

The epidermis consists of stratified squamous epithelium, i.e. it consists of layers of flattened cells. Skin, hair and nails are keratinised, meaning they have a dead, hardened hydrophobic surface made of a protein called keratin. Epidermis is made impermeable due to its contents of extracellular lipids associated with keratinocytes, especially in the middle layer of the epidermis (stratum lucidum). Mucous membranes (e.g. of the oesophagus, oral pharyngeal cavity, reproductive organs, and others) are mainly non-keratinised and moist. The epidermis has three main types of cell, namely keratinocytes (skin cells), melanocytes (pigment-producing cells) and Langerhans cells (immune cells). The Merkel cell is a fourth, less prevalent, epidermal cell.

The keratinocytes mature and differentiate with accumulation of keratin as they move outwards. They eventually fall or rub off. They form four or five distinct strata, which from the most superficial to the deepest are (i) the Stratum corneum (horny layer) with dead, dried-out hard cells without nuclei, (ii) the Stratum granulosum (granular layer) with cells containing basophilic granules and outwardly separated from stratum corneum by the thin stratum lucidum, (iii) the Stratum spinulosum (spinous, spiny or prickle cell layer) in which the cells become increasingly flattened as they move upward and (iv) the Stratum basale (basal layer) with columnar (tall) regenerative cells.

Immediately below the epidermis is the basement membrane, a specialised structure that lies between the epidermis and dermis.

The dermis is the fibrous connective tissue or supportive layer of the skin. The major fibres are collagen fibres and elastin which are interwoven.

The subcutis is the fat layer immediately below the dermis and epidermis. It is also called subcutaneous tissue, hypodermis or panniculus. The subcutis mainly consists of fat cells (adipocytes), nerves and blood vessels.

New epithelial skin cells are created in the skin's lower layer, the stratum granulosum. Over time, cells migrate to the surface of the skin and become more acidic. During their 30 day journey, they die and become saturated with keratin. Keratin and associated lipids are important because they protect the skin from outside elements.

Disease, injury, environmental factors, age, hormone levels, medication, externally applied or ingested materials, genetic conditions or a variety of other factors may lead to abnormal functioning of the skin resulting in irregularities or abnormalities. Some of these irregularities or abnormalities may be purely cosmetic in nature, e.g. dry skin, wrinkles or altered pigmentation, or may be more severe leading to pain or discomfort, e.g. eczema and psoriasis.

Dry skin is one of the most common skin conditions or abnormalities. Although certain individuals are more susceptible to dry skin, the condition can affect anyone, regardless of age, gender, or skin type.

Dry skin occurs when the skin's outer layer (the stratum corneum with the stratum lucidum) is depleted of water. When this layer is well-moistened, it minimizes water loss through the skin and helps keep out irritants, allergens, and germs. However, when the stratum corneum dries out, its protective function is reduced. This allows greater water loss, leaving skin vulnerable to environmental factors.

Under normal conditions, the stratum corneum has a water content of 10% to 30%. This water imparts to the skin its soft, smooth, and flexible texture. The water comes from the atmosphere, the underlying layers of skin, and sweat. Oil produced by skin glands and fatty substances produced by skin cells act as natural moisturizers, allowing the stratum corneum to seal in water.

The body continuously loses water from the skin's surface by evaporation. Under normal conditions, the rate of loss is slow, and the water is adequately replaced. Characteristic signs and symptoms of dry skin occur when the water loss exceeds the water replacement, and the stratum corneum's water content falls below 10%.

Moisturizers which improve or eradicate dry skin are highly desirable. Whilst many moisturizers are known in the art, there remains a need for natural products which are effective yet gentle.

Another common skin abnormality or condition is excessive amounts of the horny layer of the skin. This may result from failure of the horny layer to be sloughed off or through excessive keratin deposition in the horny layer. The former may result when the natural process of skin erosion becomes uneven, which gives skin a dry and rough character. Benign hyperproliferative disorders include epidermolytic hyperkeratosis (or cracked skin) and hair follicle keratosis. One common benign hyperproliferative condition is peripheral hypertrophy around scars and/or formation of keloids. Other hyperproliferative conditions are corns, calluses, hyperkeratotic warts (particularly veruca vulgaris), ichthyoses and palmoplantar keratoses.

Current treatments involve exfoliation or surgery in extreme cases. Hyperkeratosis is usually treated by softening the horny layer and removing the thickened skin.

Exfoliation may also be used to remove impaired epidermal cells, e.g. epidermal cells from an epidermis exhibiting a pigmentation disorder, e.g. liver spots.

Exfoliation removes the outer strata of epidermis to reveal the newer skin cells beneath. Exfoliation may be achieved by physical means (i.e. abrasion of the skin) or by chemical means. Chemical exfoliants include scrubs containing salicylic acid, glycolic acid, fruit enzymes, citric acid or malic acid and may be applied in high concentrations by a dermatologist, or in lower concentrations in over-the-counter products. Chemical exfoliation may involve the use of products that contain alpha hydroxy acids (AHAs) or beta hydroxy acids (BHAs), or enzymes that act to loosen the glue-like substances that hold the cells together at cell junctions, allowing them to ease away. This type of exfoliation is recommended for people treating acne.

The greatest disadvantage to exfoliation is the high price of some of the products and methods used to achieve it. Exfoliation will lead to some initial redness to the skin. Near the end of chemical peels, the skin will frost, with colours varying from a bright white to gray on the skin surface. More effective methods which are gentler on the skin are therefore desirable.

There thus remains a need for treatments suitable for moisturizing skin and/or for exfoliation of the horny layer of the skin.

Certain polypeptides and peptides (e.g. portions of polypeptides) which are found in fish hatching fluid have surprisingly now been found to be remarkably effective moisturizers and exfoliants. Hatching of embryos from oviparous vertebrate organisms, e.g. fish, amphibians, birds and reptiles, is facilitated by various enzymes, typically known as hatching enzymes, which are capable of partially or fully degrading the proteinaceous parts of the eggshell. Oocytes of all vertebrates have characteristic extracellular envelopes, known as vitelline envelopes, eggshells or chorion (used interchangeably herein), which are made up by the cross-linkage of various polypeptides. Proteases with different specificities act on the chorion to soften, erode and/or breakdown (i.e. degrade) the eggshell and facilitate the release of the embryo. Hence, fluid released from the egg during the hatching process and/or the fluid in which the embryo hatches (i.e. hatching fluid) comprises a multitude of polypeptides and portions of polypeptides, i.e. degradation products.

The present inventors have determined that a particular composition of fish hatching enzymes and the eggshell polypeptides generated from the degradation of the eggshell (particularly portions or fragments of said eggshell polypeptides), is particularly suitable for moisturizing skin and/or for exfoliation of the horny layer of the skin.

Hatching of embryos is achieved or facilitated, at least in part, by the so-called hatching enzymes. For instance, fish choriolysins are typically metalloproteinases found in hatching fluid. Choriolysins are generally found in two forms, namely the high choriolytic enzyme (choriolysin H, HCE) and the low choriolytic enzyme (choriolysin L, LCE), which are similar in some structural and catalytic characteristics and belong to the astacin family but with markedly different substrate preferences. Hatching enzymes with other catalytic activities have also been identified and characterized, e.g. serine proteases.

Whilst not wishing to be bound by theory, the Examples demonstrate that compositions comprising a combination of hatching enzymes, both a metalloproteinase and a serine protease, and portions of eggshell proteins from Salmonidae hatching fluid are capable of moisturizing skin and/or for exfoliation of the horny layer of the skin.

Hatching fluid from other fish contains polypeptides that are functionally equivalent to the polypeptides found in hatching fluid from Salmonidae.

It is thought that the combination of hatching enzymes and polypeptide degradation products (e.g. eggshell polypeptides and portions of said polypeptides) in the compositions defined herein may interact with different types of proteins present in the dermis and epidermis of the skin. It is believed that the unique combination of polypeptides and portions of polypeptides may work in synergy and that these interactions may be responsible for the effects of the composition in the treatment of various skin disorders or conditions.

Accordingly, at its broadest, the invention can be seen to provide a composition derivable from fish hatching fluid by a method described hereinafter. Said composition comprises a metalloproteinase, a serine protease and one or more eggshell polypeptides and/or portions of said polypeptides. In particular the composition is for use in, or in methods for, the treatment of various abnormalities, disorders or conditions of skin by moisturizing and/or exfoliating the skin as described hereinafter. In other words, the composition as described herein is for use in, or in methods for, the treatment of conditions or disorders such as dry skin, skin in which the horny layer is thicker than desirable, e.g. in hyperkeratosis conditions, or skin with undesirable pigmentation in the epidermis, e.g. liver, age, sun or brown spots. In a particularly preferred aspect, the invention may be seen as providing a composition derivable from hatching fluid, as described herein, for use in, or in methods for, the cosmetic treatment of normal but dry skin or thickened skin (such as calluses, corns or hyperkeratotic warts) or cosmetic treatment of pigmentation disorders, such as liver spots. In another preferred aspect, the invention may be seen as providing a composition derivable from hatching fluid, as described herein for use in, or in methods for, the therapeutic treatment of skin disorders or conditions, such as acne, eczema, psoriasis or warts resulting in pain. The composition referred to above is also referred to herein as a "hatching fluid extract". In addition to hatching enzymes and eggshell polypeptides and peptides, said extract may comprise native non-proteinaceous material.

It will be evident from the disclosures below that a composition derivable from fish hatching fluid, as described herein, may be provided as a pharmaceutical or cosmetic composition, which comprises one or more pharmaceutically acceptable excipients and/or diluents.

Thus, in one aspect the present invention provides a method of preparing a pharmaceutical or cosmetic composition as described herein from fish hatching fluid comprising at least the steps of:

a) suspending fish eggs in a minimal volume of water (e.g. equivalent to the volume of the eggs or less);

b) inducing synchronized, rapid hatching of said eggs, preferably such that hatching is complete within less than 6 hours for more than 80% of the embryos;

c) optionally filtering the hatched eggs to obtain hatching fluid; and d) filtering the hatching fluid of b) or c) to obtain a composition, wherein the step of filtering the hatching fluid comprises at least the steps of:

(i) filtering the hatching fluid using a filter with a pore size of at least 5 µm, preferably 5-15 µm, and particularly preferably a pore size of 7 µm, and collecting the filtrate;

(ii) optionally filtering the filtrate from step (i) using a filter with a pore size of 0.30-0.60 µm, preferably a pore size of 0.35-0.55 µm, particularly preferably 0.40-0.50 µm, most preferably 0.45 µm, and collecting the filtrate;

(iii) subjecting the filtrate from step (i) or (ii) to ion exchange chromatography comprising:

(1) loading the filtrate on to an ion exchange column, such as a DEAE (diethylaminoethyl) column;

(2) washing the column with a suitable buffer, e.g. a buffered wash solution at a pH of 7-9, e.g. comprising 20 mM Tris-HCl, pH 8.5;

(3) eluting polypeptides from the column (in particular leukolectin polypeptides) using a first elution buffer or solvent (e.g. with an ionic strength lower than the second elution buffer of step (4)), such as the buffered wash solution further comprising a salt, e.g. at a concentration of 50-100 mM, e.g. 50 mM NaCl;

(4) eluting the remaining polypeptides from the column using a second elution buffer or solvent (e.g. with an ionic strength higher than the first elution buffer of step (3)), such as the buffered wash solution comprising a higher concentration of salt than the first elution buffer, e.g. at a concentration of 500 mM to 2M, e.g. 1M NaCl;

(5) collecting the eluate from step (4);

e) exchanging the water in the eluate from step (5) with a pharmaceutically (or cosmetically) acceptable buffer;

f) filtering the solution obtained from step (e) using a filter with a pore size of 0.15-0.30 μm, preferably a pore size of 0.22 μm and collecting the filtrate; and g) preparing said pharmaceutical or cosmetic composition from the filtrate from step (f).

As referred to herein, "hatching fluid" is the fluid released from eggs during the process of hatching and may be in a crude, diluted or filtered form. The crude hatching fluid refers to undiluted, untreated fluid. Diluted hatching fluid refers to hatching fluid which may have been mixed with other fluid during or after hatching, e.g. when hatching occurs in water.

The present invention also provides a pharmaceutical or cosmetic composition obtained or obtainable by the method described herein.

The step of subjecting the filtrate to ion exchange chromatography may be performed using any suitable method that results in a filtrate in which the polypeptides in the composition of the invention (including portions thereof as defined below) are enriched relative to at least one of the other polypeptides present in the hatching fluid extract prior to purification (i.e. prior to ion exchange chromatography). For instance, ion exchange chromatography may result in an final eluate (i.e. an eluate obtained using the second elution buffer) in which the hatching enzymes and eggshell polypeptides in the hatching fluid are enriched by at least 5% relative to at least one of the other polypeptides present in the hatching fluid, preferably all of the other polypeptides, present in the hatching fluid extract prior to this step of purification. Other polypeptides may be defined as polypeptides that do not fall within the structural and/or functional definition of a polypeptide in the composition for use in the methods of the invention (i.e. a hatching enzyme or eggshell polypeptide or portion thereof) as defined herein. The pharmaceutical or cosmetic composition of the invention (i.e. obtained or obtainable by the method described herein) does not contain leukolectin polypeptides, which are defined further below. Preferably, the polypeptides are enriched by at least 10, 20, 30, 40 or 50% by this step. Especially preferably the polypeptides are purified to a degree of purity of more than 50 or 60%, e.g. >70, 80 or 90%, preferably more than 95 or 99% purity relative to at least one of the other polypeptides present in the hatching fluid extract prior to purification, e.g. leukolectin. Thus, the eluate may comprise only trace amounts of other polypeptides, such as leukolectin, that are present in the hatching fluid prior to ion exchange chromatography, e.g. less than 0.1%, 0.01%, 0.001%, 0.0001% or 0.00001% w/w.

Ion exchange chromatography is well known in the art and suitable ion exchange columns are commercially available. In an exemplary embodiment the ion exchange column is a DEAE (diethlyaminoethyl) column, i.e. a column of an inert matrix, such as cellulose, silica, sepharose etc. which has been coupled to DEAE. However, other ion exchange columns may be suitable for use in the method described above.

The step of loading the filtered hatching fluid on to the ion exchange column comprises applying the hatching fluid to an ion exchange column that has been prepared or activated such that it is capable of binding the polypeptides in the composition of the invention. Preparing or activating the ion exchange column typically involves washing the column with a buffer, e.g. the wash buffer as defined below. This pre-wash step results in an ion exchange column which is under optimum conditions, e.g. pH, to enable the polypeptides to bind to the column. Thus, the loading step may be viewed as a step of binding the polypeptides of the composition of the invention to an ion exchange column.

Following the step of loading the filtered hatching fluid on to the ion exchange column, and in accordance with standard protocols, the column may be washed with a suitable buffer to remove unwanted components present in the hatching fluid that are not bound to the column. Washing comprises applying a volume of wash buffer to the column, typically the volume of wash buffer applied to the column is at least equal to the volume of the ion exchange column and may be more, e.g. at least 1.5, 2, 3, 4 or 5 times the volume of the column. In some embodiments the wash step may be repeated, e.g. 2, 3, 4, 5 or more times. Any suitable wash buffer may be utilised in the method of the invention. A suitable wash buffer is one that does not disrupt significantly the interaction between the polypeptides of interest and the ion exchange column, e.g. less than 10%, e.g. less than 5, 4, 3, 2 or 1%, of the polypeptides of the composition of the invention is removed from the ion exchange column by each wash step. In a preferred embodiment the wash buffer is a solution of Tris-HCl in the range of 10-100 mM, preferably 10-50 mM, e.g. 20-30 mM, with a pH in the range of 6-10, preferably 7-9, e.g. 8.5. The flowthrough from the wash step may be collected, e.g. to determine whether further wash steps are required (e.g. tested for the presence of polypeptides, polysaccharides, salts etc that represent unwanted components present in the hatching fluid prior to purification) and/or discarded.

The step of eluting the leukolectin polypeptides from the ion exchange column (the "first" elution step) may be performed by any suitable means and typically involves the application of a solvent or solution to the column to disrupt the interaction between at least the leukolectin polypeptides and the ion exchange column, i.e. a first elution solution (e.g. buffer) or solvent. However, the first elution solvent or solution is not sufficient to disrupt the interaction between the polypeptides of interest and the ion exchange column, e.g. less than 10%, e.g. less than 5, 4, 3, 2 or 1%, in total of the polypeptides of the composition of the invention is removed from the ion exchange column by the elution step to elute the leukolectin polypeptides. Typically the volume of first elution buffer or solvent applied to column is at least equal to the volume of the ion exchange column and may be more, e.g. at least 1.5, 2, 3, 4 or 5 times the volume of the column. In some embodiments the "first" elution step (i.e. using the first elution solution or solvent) may be repeated, e.g. 2, 3, 4, 5 or more times. The eluate containing the leukolectin polypeptides (the flowthrough from the "first" elution step) may be collected from each elution step. Alternatively or additionally, the eluate containing the leukolectin polypeptides is discarded. A suitable first elution buffer or solvent is one which disrupts the interaction between the leukolectin polypeptides and the ion exchange column, e.g. at least 70%, preferably at least 75, 80, 85, 90, 95 or 99%, of the leukolectin polypeptides bound to the column is eluted from the column by each elution step.

In a preferred embodiment the first elution buffer is the same as the wash buffer also comprising a substance capable of disrupting the interaction between the leukolectin polypeptides and the ion exchange column, e.g. a salt, to provide a low ionic strength (relative to the second elution buffer). The salt may be present in the range of 10-500 mM, preferably 20-400 mM, 30-300 mM, 40-200 mM or 50-100 mM, e.g. 50 mM NaCl. Thus, in some embodiments the elution buffer is a solution of Tris-HCl in the range of 10-100 mM, preferably 10-50 mM, e.g. 20-30 mM, with a pH in the range of 6-10, preferably 7-9, e.g. 8.5 also comprising a salt, e.g. NaCl, KCl etc. in a range as described above.

The step of eluting the polypeptides of the composition of the invention from the ion exchange column (the "second" or "final" elution step) may be performed by any suitable means and typically involves the application of a solvent or solution to the column to disrupt the interaction between the polypeptides of interest and the ion exchange column. Typically the volume of elution buffer or solvent applied to column is at least equal to the volume of the ion exchange column and may be more, e.g. at least 1.5, 2, 3, 4 or 5 times the volume of the column. In some embodiments the "second" elution step (i.e. the step using the second elution solution or solvent) may be repeated, e.g. 2, 3, 4, 5 or more times. The eluate may be collected from each elution step and one or more of the eluates may be combined prior to the step of exchanging the water in the eluate. A suitable elution buffer or solvent is one which disrupts the interaction between the polypeptides of the composition of the invention and the ion exchange column, e.g. at least 70%, preferably at least 75, 80, 85, 90, 95 or 99%, of the polypeptides of the composition of the invention bound to the column is eluted from the column by each "second" elution step.

In a preferred embodiment the second elution buffer is the same as the wash buffer also comprising a substance capable of disrupting the interaction between the polypeptides of interest and the ion exchange column, e.g. a salt, to provide a higher ionic strength than the first elution buffer. The salt may be present in the range of 500-2000 mM, preferably 600-1800 mM, 700-1700 mM, 800-1500 mM or 900-1200 mM, e.g. about 1000 mM NaCl. Thus, in some embodiments the elution buffer is a solution of Tris-HCl in the range of 10-100 mM, preferably 10-50 mM, e.g. 20-30 mM, with a pH in the range of 6-10, preferably 7-9, e.g. 8.5 also comprising a salt, e.g. NaCl, KCl etc. in a range as described above.

The step of exchanging the water in the filtrate may be performed using any suitable method known in the art, e.g. diafiltration or dialysis. In a particularly preferred embodiment, this step is performed using diafiltration using a filter with an exclusion size of less than 12 kDa, preferably 10 kDa or less, e.g. 9, 8, 7, 6, 5, 4, 3 kDa or less.

Diafiltration uses ultrafiltration membranes to remove e.g. salts or other unwanted or undesirable microsolutes from a solution or as a way of exchanging the solvent, e.g. buffer, of a solution. Small molecules are separated from a solution while retaining larger molecules in the retentate (the material which does not pass through the filter). Microsolutes and solvents, e.g. water, are generally easily washed through the membrane. Typically about 3 volumes of diafiltration solvent (e.g. phosphate buffered saline) will eliminate 95% of the microsolute. Thus, the above filtrate, i.e. elulate, from step (5) is initially processed by diafiltration and this results in the concentration of the retentate as a proportion of the solution (which contains the soluble impurities/unwanted fraction of the hatching fluid) passes through the membrane. The retentate is then diluted with a pharmaceutically acceptable buffer, e.g. 0.5 mM Sodium phosphate and 1 mM Sodium chloride, phosphate buffered saline etc. The diluted retentate may be subjected to repeated rounds of diafiltration, if necessary. Typically, prior to step (f) the retentate is diluted such that the filtrate from step (f) has an enzymatic activity of 25000-45000 mU/L, preferably 25000-35000 mU/L and most preferably about 30000 mU/L. The enzymatic activity of the filtrate may be measured by the capacity of the filtrate to cleave the Factor Xa chromogenic substrate ($CH_3OCO$-D-CHA-Gly-Arg-pNA-AcOH, Sigma aldrich product number: F3301-25MG). Prior to the step of diafiltration the hatching fluid may comprise an enzymatic activity in the range of 90 to 1,300,000 mU/L. One unit (1 U) may be defined as the amount of the enzyme required to catalyze the conversion of 1 μmol of substrate per minute.

The Factor Xa chromogenic substrate (Sigma-Aldrich) is cleaved by the serine protease enzyme present in the hatching fluid yielding a yellow product that can be measured conveniently using spectrophotometrical analysis at a wavelength of 405 nm. A typical assay comprises the addition of 100 μl hatching fluid solution, obtainable from step (d) or (e) of the above method, to 600 μl substrate solution, comprising 10 μl Factor Xa chromogenic substrate (10 mg/ml in milli-q or distilled water), 70 μl 0.2 M Tris-HCl pH 8.5 and 520 μl $dH_2O$. Conveniently the change in absorbance may be measured for 5-20 minutes (or up to an hour for samples with low enzymatic activity), typically 10 minutes. The result is multiplied with an appropriate factor, e.g. 10 (for a 10 minute assay) to get the enzyme activity per 1 ml of sample. Other appropriate and equivalent substrates may be used to determine the activity of the hatching fluid.

As mentioned above, in some embodiments it may be advantageous to synchronize the step of egg hatching to maximize the amount of hatching fluid obtained, particularly the amount of the desired polypeptides or portions thereof in the hatching fluid, for purification. Synchronized hatching may be achieved by any suitable method known in the art. For instance, some eggs may be synchronized using photomanipulation, e.g. transferring eggs from the light (which inhibits hatching) in to conditions with no light. Manipulation of the temperature of the eggs, e.g. the temperature of the solution in which the eggs hatch, deoxygenation of the hatching environment, e.g. deoxygenation of the solution in which the eggs hatch (Oppen-Berntsen et al. 1990, Aquaculture, 86, pp. 417-430), increasing the amount of carbon dioxide in the hatching environment, and stimulation of the eggs using electricity can also be used to cause synchronized hatching. In some embodiments, synchronized hatching may be achieved using pheromones, e.g. peptide pheromones capable of affecting, i.e. stimulating, embryo development and hatching. As noted above, the eggs may be suspended in a minimal volume of water, which may be equivalent to the volume of eggs or less, e.g. for every 1 ml of eggs a suspending liquid of 51, 0.75, 0.5, 0.25 ml may be used, e.g. from 0.5 to 1 ml. In some embodiments it may be advantageous to dilute the hatching fluid to facilitate the subsequent purification steps, e.g. to reduce the viscosity of the hatching fluid. Thus, the method may comprise a further step of diluting the hatching fluid. Preferably the filtrate may be diluted by a factor of at least 0.1, 0.2, 0.5, 0.75, 1.0, 1.5, 2, 3, 4, 5, 10, 15, 20, 50, 100, 1000, 5000 or 10000.

In preferred embodiments synchronized, rapid hatching of said eggs, is such that hatching is complete within less than 6 hours for more than 80% of the embryos. In particularly preferred embodiments, hatching is complete within less than 5, 4, 3 or 2 hours, such as 0.5-6 hours, 1-5 hours, 1.5-4 hours, 2-3 hours, e.g. 1-2 hours. Furthermore, in some embodiments hatching is complete within the periods stated above for more than 85%, 90%, or 95% of the embryos, e.g. more than 90, 91, 92, 93, 94, 95, 96, 97, 98 or 99% of the embryos.

The method of preparing a pharmaceutical or cosmetic composition described above results in an enriched preparation which is preferably substantially free of any contaminating components derived from the source material or material used in the isolation procedure, e.g. components other than the polypeptides or portions of polypeptides comprised in the crude hatching fluid. Other contaminating components include leukolectin polypeptides. In a preferred embodiment the composition may be enriched to a degree of purity of more than 30, 40, 50 or 60%, e.g. >70, 80 or 90%, purity as assessed w/w (dry weight) of the polypeptides and portions of polypeptides of interest in comparison to the starting hatching fluid, i.e. 90% purity refers to a loss of 90% of the starting material (contaminating components) through the course of the method of preparation. However, compositions may be used which have lower purity, e.g. retain more than 40, 50, 60, 70, 80 or 90% of the starting material. However, even compositions of lower purity do not contain leukolectin peptides, i.e. less than 0.0005% [w/w], preferably less than 0.0001, 0.00005 or 0.00001% [w/w].

Whilst the filtrate from step (f) may itself form the pharmaceutical or cosmetic composition, optionally the product (the filtrate of step (f)) obtained or obtainable from the above method may be diluted (or concentrated) to an appropriate concentration in step (g) to produce the pharmaceutical or cosmetic composition and/or prior to its use in the methods and uses of the invention. Thus, the method may comprise a further step of diluting (or concentrating) the composition. Preferably the filtrate may be diluted (or concentrated) by a factor of at least 1.5, 2, 3, 4, 5, 10, 15, 20, 50, 100, 1000, 5000 or 10000. Particularly preferably the final composition comprises 0.5-10%, e.g. 0.5-5%, preferably 0.5-3% (e.g. 1 or 3%) of the filtrate of step (f). In a particularly preferred embodiment, the solution from step (e) of the above method is diluted or concentrated to achieve a solution with an enzymatic activity of 10000-100000 mU/L as measured by the above described method. Preferably the solution, and therefore the filtrate from step (f) comprises an activity of 20000-90000, 25000-80000, 25000-60000, 25000-50000, 25000-45000 or 25000-35000 mU/L. Most preferably the solution comprises an activity of about 30000 mU/L.

Optionally, one or more pharmaceutically acceptable excipients and/or diluents may be added to the composition obtained or obtainable from the above method. Thus, step (g) of preparing a pharmaceutical or cosmetic composition from the filtrate from step (f) may comprise a step of adding one or more pharmaceutically acceptable excipients and/or diluents to the composition or combining the composition with one or more pharmaceutically acceptable excipients and/or diluents. Alternative or additional preparation method steps include changing or modifying the solvent, e.g. pH, ion concentration etc.

Other pharmaceutically acceptable components or ingredients may be added to the composition obtained or obtainable from the above method e.g. during step (g). The one or more other components may be active components, i.e. components that have an effect on the skin, preferably that are also useful in the treatment of a condition or disorder of the skin, e.g. in the conditions or disorders described herein. Thus, alternatively or additionally, the method may comprise a further step of adding one or more pharmaceutically acceptable active components to the composition or combining the composition with one or more pharmaceutically acceptable active components in step (g). Pharmaceutically acceptable active components may include minerals, vitamins, enzymes, proteins, peptides, amino acids, lipids, antioxidants, polysaccharides, substances suitable as sunscreen filters, chemical exfoliants, extracts and mixtures thereof, as described in more detail below.

The pharmaceutical or cosmetic composition obtained or obtainable from the above methods is suitable for use in the methods of the invention, as described elsewhere herein.

The pharmaceutical or cosmetic composition of the invention comprises a combination of hatching enzymes and eggshell polypeptides or portions of polypeptides that are particularly useful in the treatment of various skin conditions or disorders.

In particular, the compositions of the invention comprise a hatching enzyme with metalloproteinase activity, a hatching enzyme with serine protease activity and one or more eggshell polypeptides or portions thereof, preferably wherein said portions are structurally equivalent to portions generated by proteolytic cleavage of the polymerized and cross-linked eggshell or chorion by hatching enzymes during hatching. The polypeptides may be referred to herein as the polypeptides of interest.

The sequence of an exemplary metalloproteinase that may be present in the compositions of the invention is presented in SEQ ID No. 1.

An exemplary serine protease that may be present in the composition of the invention may be defined as a polypeptide with a molecular weight of around 28 kDa that has the following properties:

a) cleaves chromozym X;
b) is inhibited by benzamidine;
c) cleaves peptide bonds with arginine;
d) remains active in the presence of 8M urea, molar concentrations of salt, distilled water and organic solvents, preferably dioxane or propanol; and
e) retains enzymatic activity in solution at room temperature for 50 days. Preferably the serine protease is obtainable in a purified form by a method comprising the steps of:

a) suspending fish, e.g. salmon, eggs in a minimal volume of water;
b) inducing synchronized, rapid hatching of said eggs;
c) filtering the hatched eggs to obtain hatching fluid;
d) adding solid urea to said hatching fluid to allow dissociation of eggshell fragments and subjecting said fluid to low speed centrifugation;
e) further purifying said serine protease by subjecting the centrifugation supernatant to gel filtration; and
f) further purifying said serine protease by affinity chromatography on a Benzamidine-modified Superose 6B® column, wherein said affinity chromatography is performed by performing concentrated salt washes followed by elution with dioxane, in concentrated salt solution, to extract polypeptides with serine protease activity bound to the chromatography matrix or to macromolecular structures.

Eggshell polypeptides are structural proteins which are cross-linked to form chorion. Eggshell polypeptides and portions thereof are present in hatching fluid via the degradation of the eggshell. In some embodiments, eggshell polypeptides found in the composition of the invention are preferably acidic or very acidic, e.g. have a pI from 3 to 5.5, preferably from 3.5 to 5.2.

Eggshell polypeptides appear in hatching fluid in various forms, particularly in the form of portions or fragments of the full-length polypeptides. As full-length eggshell polypeptides comprise the portions that are present in hatching fluid it is envisaged that both full-length eggshell polypeptides and portions thereof will find utility in the present invention. Furthermore, various isoforms of eggshell polypeptides and their portions have been identified in hatching fluid.

We disclose herein three exemplary eggshell polypeptides which may be present in the compositions of the invention. The sequences of some eggshell polypeptides found in hatching fluid have been determined by mass spectroscopy and are presented in SEQ ID Nos. 2-4. These sequences represent portions or fragments of polypeptides derived from the full-length eggshell polypeptides, which are presented in SEQ ID Nos. 8, 6 and 7, respectively. Hence, SEQ ID Nos. 2-4 may be defined as portions of eggshell polypeptides as defined herein.

As discussed above, each eggshell polypeptide or portion thereof may exist in various isoforms.

Thus, components of the pharmaceutical or cosmetic composition obtained or obtainable by the method described above may be defined as:

(i) a metalloproteinase comprising an amino acid sequence as set forth in SEQ ID No. 1 or a sequence which is at least 70% identical to said sequence;

(ii) a serine protease which is obtainable by the method described above; and (iii) an eggshell polypeptide selected from any one or more of:

(a) an eggshell polypeptide comprising an amino acid sequence as set forth in SEQ ID No. 2 or a sequence which is at least 70% identical to said sequence;

(b) an eggshell polypeptide comprising an amino acid sequence as set forth in SEQ ID No. 3 or a sequence which is at least 70% identical to said sequence; and (c) an eggshell polypeptide comprising an amino acid sequence as set forth in SEQ ID No. 4 or a sequence which is at least 70% identical to said sequence; or (iv) a portion of any of the polypeptides defined in (i) to (iii) which portion has a length as described hereinafter;

and one or more pharmaceutically acceptable excipients and/or diluents. (Said at least 70% sequence identity is preferably at least 80, 90, 95, 96, 97, 98 or 99% identity.)

As mentioned above, in some embodiments longer sequences than those presented in SEQ ID Nos. 2-4 may exist in the composition. Thus, in the above list, SEQ ID Nos. 2-4 may be replaced with SEQ ID Nos. 5-7, respectively and wherein SEQ ID NO: 2 can alternatively be replaced with SEQ ID NO: 8.

As mentioned above, the pharmaceutical or cosmetic composition described herein does not comprise a functional leukolectin polypeptide or a functional portion thereof. A leukolectin polypeptide may be defined as a polypeptide comprising an amino acid sequence as set forth in any one of SEQ ID Nos. 9-12 or a sequence which is at least 50% identical to said sequence, or a portion of any of said sequences.

A functional leukolectin polypeptide is a polypeptide that is capable of inhibiting the release of matrix metalloproteinases (MMPs), which are zinc dependent endopeptidases, from dermal fibroblasts. Hence, a polypeptide that falls within the structural definition of a leukolectin polypeptide defined above may be considered to be a non-functional leukolectin polypeptide if it has less than 50, 40, 30, 20, 10, or 5% of the activity of a functional leukolectin, e.g. any one of SEQ ID Nos. 9-12, as defined by the capacity of the polypeptides to inhibit of the release of MMPs in in vitro cell cultures. Alternatively expressed, a functional leukolectin polypeptide must have at least 50, 70, or 90% of the activity of a functional leukolectin, e.g. any one of SEQ ID Nos. 9-12, as defined by the capacity of the polypeptides to inhibit of the release of MMPs in in vitro cell cultures.

The total concentration of the polypeptides or portions thereof defined herein in the compositions defined herein may vary. However, in a preferred embodiment the proportion of each type of polypeptide or groups of polypeptides is consistent for all compositions, i.e. irrespective of the total polypeptide concentration. In particularly preferred embodiments the proportion of polypeptides defined hereinbefore in the composition as a percentage of the total polypeptides in the composition may be defined as:

(i) about 0.05 to about 0.20% [w/w] metalloproteinase, preferably about 0.100% to about 0.125%, such as about 0.108% to about 0.112% metalloproteinase;

(ii) about 0.15% to about 0.40% [w/w] serine protease, preferably about 0.255% to about 0.310%, such as about 0.275% to about 0.290% serine protease; and (iii) about 99.40% to about 99.80% [w/w] total eggshell polypeptides or portions of said polypeptides, preferably about 99.575% to about 99.645%, such as about 99.598% to about 99.617% total eggshell polypeptides or portions of said polypeptides.

As referred to herein said total eggshell polypeptides or portions thereof include both eggshell polypeptides defined hereinbefore and other very acidic eggshell proteins which are obtainable by precipitation of polypeptides associated with eggshells with 4 times volume of acetone and have a pI of from 3 to 5.5.

Thus, the proportion of any one eggshell polypeptide or portion of said polypeptide in the composition of the invention may be about 0-99.80% [w/w] of the total polypeptides in the composition, such as 1-95%, 2-90%, 3-85%, 4-80%, 5-75%, 10-70%, 15-65%, 20-55%, 25-50% or 30-40%, wherein the total proportion of eggshell polypeptides or portions of said polypeptides in the composition does not exceed 99.80% of the total polypeptides in the composition. Preferably, the total proportion of eggshell polypeptides or portions of said polypeptides in the composition does not exceed 99.617% of the total polypeptides in the composition.

References to a pharmaceutical composition herein may be read as encompassing cosmetic compositions.

"Polypeptides" as referred to herein are molecules with preferably more than 50, 100, 150, 200 or 250 residues and/or less than 500, 400, 300, 200 or 100 residues or a range selected therefrom. As referred to herein a "portion" preferably comprises at least 30, 40, 50, 60, 70, 80, 90, 100, 110, 120, 130, 140, 150, 160, 170, 180, 190, 200, 210, 220, 230, 240 or more amino acids of the sequence from which it is derived. Said portion may be obtained from a central or N-terminal or C-terminal portions of the sequence. Preferably said portion is obtained from the N-terminal end, e.g. from the first 50, 100 or 150 residues of the polypeptide. Alternatively preferred are portions obtained from the C-terminal end, e.g. from the last 50, 100 or 150 residues of the polypeptide.

Preferably the polypeptide sequences defined herein are at least 55, 60, 65, 70, 75, 80, 85, 90, 95, 96, 97, 98 or 99% identical to the sequence (SEQ ID Nos 1-12) to which it is compared.

Sequence identity may be determined by, e.g. using the SWISS-PROT protein sequence databank using FASTA pep-cmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 200, 100 or 50 contiguous amino acids.

Preferably such sequence identity related polypeptides are functionally equivalent to the polypeptides which are set forth in the recited Sequence Nos. Such functionally equivalent polypeptides may take the form of derivatives as set forth below.

Furthermore, "portions" as described herein may be functional equivalents. Preferably these portions satisfy the identity (relative to a comparable region) conditions mentioned herein.

As referred to herein, to achieve "functional equivalence" the polypeptide may show some reduced efficacy in performing the enzymatic activity and/or pharmaceutical or cosmetic function relative to the parent molecule (i.e. the molecule to which it is related by sequence identity), but preferably is as efficient or is more efficient. Thus, functional equivalence relates to a polypeptide which is effective in the treatment of a disorder or condition of the skin as described hereinafter. This may be tested by comparison of the effects of the derivative (i.e. sequence related) polypeptide relative to the polypeptide to which it is related in a qualitative or quantitative manner, e.g. by performing the in vivo analyses referred to in the Examples. Where quantitative results are possible, the derivative is at least 30, 50, 70 or 90% as effective as the parent polypeptide. Alternatively or additionally in vitro testing may be performed, e.g. by analysis of the capacity of the hatching enzymes to cleave suitable polypeptide or peptide substrates, such as Factor X, e.g. metalloproteinase or serine protease substrates.

Particularly preferred functionally-equivalent variants are natural biological variations (e.g. allelic variants or geographical variations within a species or alternatively in different genera, e.g. fish).

Accordingly, in a preferred embodiment, suitable fish, particularly fish eggs, from which the compositions of the invention may be obtained (i.e. starting material from which polypeptides contained in the compositions and the compositions of the invention may be obtained) include any fish of the Teleostei infraclass, which is one of three infraclasses of the class Actinopterygii. Hence, the fish may be selected from a fish of any Superorder selected from the list consisting of Osteoglossomorpha, Elopomorpha, Clupeomorpha, Ostariophysi, Protacanthoptetygii, Stenoptetygii, Cyclosquamata, Scopelomorpha, Lampridiomorpha, Polymyxiomorpha, Paracanthopterygii and Acanthoptetygii.

In some embodiments, the fish may be selected from a fish of any Order selected from the list consisting of Osteoglossiformes, Hiodontiformes, Elopiformes, Albuliformes, Notacanthiformes, Anguilliformes, Saccopharyngiformes, Clupeiformes, Gonorynchiformes, Cypriniformes, Characiformes, Gymnotiformes, Siluriformes, Argentiniformes, Salmoniformes, Esociformes, Osmeriformes, Ateleopodiformes, Stomiiformes, Aulopiformes, Myctophiformes, Lampriformes, Polymixiiformes, Percopsiformes, Batrachoidiformes, Lophiiformes, Gadiformes, Ophidiiformes, Mugiliformes, Atheriniformes, Beloniformes, Cetomimiformes, Cyprinodontiformes, Stephanoberyciformes, Beryciformes, Zeiformes, Gobiesociformes, Gasterosteiformes, Syngnathiformes, Synbranchiformes, Tetraodontiformes, Pleuronectiformes, Scorpaeniformes Perciformes and Acipenseriformes.

In preferred embodiments the fish may be selected from a fish of any Order selected from the list consisting of Salmoniformes, Cypriniformes, Perciformes, Siluriformes, Mugiliformes and Acipenseriformes.

In particularly preferred embodiments the fish may be selected from a fish of any Family selected from the list consisting of Salmonidae, Cyprinidae, Cichlidae, Pangasiidae, Sciaenidae, Serranidae, Carangidae, Sparidae, Lateolabracidae, Moronidae, Mugilidae, Latidae, Eleotridae and Acipenseridae.

Thus, in some embodiments, the fish may be a bonytongued fish, a mooneye, a goldeye, a ladyfish, a tarpon, a bonefish, a halosaur, a spiny eel, a true eel, a gulper, a gulper eel, a herring, an anchovy, a milkfish, a barb, a carp, a danio, a goldfish, a loach, a minnow, a rasbora, a characin, a pencilfish, a hatchetfish, a piranha, a tetra, an electric eel, a knifefish, a catfish, a barreleye, a slickhead, a salmon, a trout, a pike, a smelt, a galaxiid, a jellynose fish, a bristlemouth, a marine hatchetfish, a Bombay duck fish, a lancetfish, a lanternfish, an oarfish, an opah, a ribbonfish, a beardfish, a cavefish, a trout-perch, a toadfish, an anglerfish, a cod, a pearlfish, a Silver arowana, a mullet, a silverside, a rainbowfish, a flyingfish, a whalefish, a livebearer, a killifish, a ridgehead, a fangtooth, a pineconefish, a dory, a clingfish, a stickleback, a pipefish, a seahorse, a swamp eel, a filefish, a pufferfish, a flatfish, a scorpionfish, a sculpin, an anabantid, a bass, a cichlid, a goby, a gourami, a mackerel, a perch, a scat, a whiting or a wrass.

In particularly preferred embodiments the fish may be any species selected from Grass carp (*Ctenopharyngodon idella*), Silver carp (*Hypophthalmichthys molitrix*), Catla (*Catla catla*), Common carp (*Cyprinus carpio*), Bighead carp (*Hypophthalmichthys nobilis*), Crucian carp (*Carassius carassius*), Nile tilapia (*Oreochromis niloticus niloticus*), Pangas catfish (*Pangasius pangasius*), Roho labeo (*Labeo rohita*), Atlantic salmon (*Salmo salar*), Large yellow croaker (*Larimichthys crocea*), Greasy grouper (*Epinephelus tauvina*), Sea trout (*Salmo trutta trutta*), Japanese amberjack (*Seriola quinqueradiata*), Gilthead seabream (*Sparus aurata*), Japanese seabass (*Lateolabrax japonicus*), European seabass (*Dicentrarchus labrax*), Silver seabream (*Chrysophrys auratus*), Flathead grey mullet (*Mugil cephalus*), Barramundi (*Lates calcarifer*), Marble goby (*Oxyeleotris marmorata*), Mozambique tilapia (*Oreochromis mossambicus*), Salmon trout (*Oncorhynchus mykiss*), Coho salmon (*Oncorhynchus kisutch*), Chinook salmon (*Oncorhynchus tshawytscha*), Pink salmon (*Oncorhynchus gorbuscha*), Chum salmon (*Oncorhynchus keta*), Sockeye salmon (*Oncorhynchus nerka*), Siberian sturgeon (*Acipenser baerii*) and Danube sturgeon (*Acipenser gueldenstaedtii*).

In some embodiments, the pharmaceutical or cosmetic compositions may be obtained or obtainable from hatching fluid from more than one type of fish, particularly more than one type of fish egg, i.e. fish eggs from any one or more of the fish defined above. For instance, the hatching fluid from two or more types of fish egg could be used in the method described herein to obtain the pharmaceutical or cosmetic composition of the invention. Hence, the method of the invention may include a step of combining the hatching fluid collected from the hatched eggs of one or more organisms, e.g. before or after filtration.

By "pharmaceutically acceptable", "physiologically acceptable" or "cosmetically acceptable" is meant that the ingredient must be suitable for therapeutic and/or cosmetic applications and compositions. The ingredients also must be compatible with other ingredients in the composition as well as physiologically acceptable to the recipient.

The active ingredients, i.e. the polypeptide components of the composition obtainable by the method described above, for administration may be appropriately modified for use in a pharmaceutical or cosmetic composition. For example the composition used in accordance with the invention may be stabilized against degradation for example by the use of appropriate additives such as salts or non-electrolytes, acetate, SDS, EDTA, citrate or acetate buffers, mannitol, glycine, HSA or polysorbate.

The polypeptide components obtained or obtainable by the methods described herein may be present in the compositions for the therapeutic or cosmetic uses as the sole active ingredients or may be combined with other ingredients, particularly other active ingredients, e.g. to augment the therapeutic or cosmetic effect (as described above) or to make the composition more appealing to the consumer.

The composition described herein may also comprise impurities, e.g. after the preparation of said composition from one of the above described natural sources. In compositions as described herein, the various polypeptides or portions of polypeptides derivable from fish hatching fluid (i.e. total polypeptide component) may be present (in combination) in the range 0.001 to 50% w/w of the composition prepared according to the above described method (or 10-100 fold lower if the composition is diluted in step (g)). Preferably said polypeptides or portions of polypeptides derivable from fish hatching fluid are present (in combination) at a range of 0.0005 to 10% w/w of the composition (or up to 10-40%), e.g. 0.001 to 5%, 0.001 to 3%, 0.001 to 2%, 0.001 to 1%, 0.001 to 0.5%, 0.001 to 0.15% w/w of the composition prepared according to the above method (e.g. at 0.05-0.5% w/w or 0.0005-0.005% w/w if diluted in the final step). Accordingly, individual polypeptides or portions of polypeptides derivable from fish hatching fluid may be present at the range of $1\times10^{-5}$ to 10% w/w of the composition. In some embodiments said individual polypeptides or portions of polypeptides derivable from fish hatching fluid may be present at the range $1\times10^{-5}$ to 5% w/w of the composition, e.g. $1\times10^{-5}$ to 4%, $1\times10^{-5}$ to 3%, $1\times10^{-5}$ to 2%, $1\times10^{-5}$ to 1%, $1\times10^{-4}$ to 0.5%, $1\times10^{-4}$ to 0.15%, $1\times10^{-4}$ to 0.1% or $1\times10^{-4}$ to 0.01% w/w of the pharmaceutical or cosmetic composition if not further diluted in step (g), or reduced by a factor, e.g. 10-200, e.g. 30-100 if diluted in step (g).

The proportion of the polypeptides or portions of polypeptides derivable from fish hatching fluid in the compositions may be defined relative to the other solutes in the composition, i.e. excluding solvents, e.g. water. Thus, said polypeptides or portions of polypeptides, in combination, may be present at the range of 1-100% w/w of the dry mass of the composition. In some embodiments the polypeptides or portions of polypeptides, in combination, may be present at the range of 1-90% w/w of the dry mass of the composition, e.g. 5-80%, 10-75%, 20-70%, 30-65% w/w, e.g. about 68 or 69% w/w, of the dry mass of the composition. Thus, individual polypeptides or portions of polypeptides may be present at the range of 0.001 to 80% w/w of the dry mass of the composition, e.g. 0.0001 to 75%, 0.001 to 70%, 0.01 to 60% w/w, 0.05 to 50% w/w of the dry mass of the composition. As described herein the composition may be diluted for use according to the invention in step (g).

In a further aspect of the invention, the compositions as described herein are for use in therapy.

As mentioned above, the polypeptides or portions of said polypeptides in the composition of the invention exhibit therapeutic properties in the treatment of skin abnormalities, disorders or conditions, by moisturizing and/or exfoliating the skin.

Preferred skin abnormalities, conditions or disorders to be treated are dry skin, skin in which the horny layer is thicker than desirable, e.g. in hyperkeratosis conditions, or skin with undesirable pigmentation in the epidermis, e.g. liver, age, sun or brown spots. The treatments may be cosmetic, e.g. the treatment of normal but dry skin or thickened skin (such as calluses, corns or hyperkeratotic warts) or treatment of pigmentation disorders, such as liver spots, or therapeutic, e.g. to treat acne, eczema, psoriasis or warts resulting in pain.

As referred to herein a "disorder" refers to an underlying pathological disturbance in a symptomatic or asymptomatic organism relative to a normal organism, which may result, for example, from infection or an acquired or congenital genetic imperfection. An "abnormality" or "condition" refers to an irregularity or defect in the skin relative to normal optimal skin but which is not as the result of a pathological disturbance. The defect/irregularity may instead result from age, injury, environmental factors, hormone levels, medication, externally applied or ingested materials, genetic conditions or a variety of other factors which leads to abnormal functioning of the skin resulting in irregularities.

The disorder, abnormality or condition may be merely cosmetic or non-cosmetic requiring medical treatment, or a combination thereof.

As referred to herein "cosmetic" is intended to refer to a treatment which does not cure, treat or prevent a disease or disorder, but instead serves as a skincare product or to modify or improve the appearance of the skin, e.g. the colour, texture or moisture content of the skin.

A "non-cosmetic" (or medical) ingredient used in medical treatments as described herein serves to cure, mitigate, treat or prevent one or more symptoms of the disorder, e.g. pain or discomfort.

The basis of the treatments described herein is the skin moisturizing and exfoliating effects of the hatching enzymes and eggshell polypeptides as disclosed herein. These effects have been shown in the Examples provided herein.

Thus treatments based on the moisturizing and/or exfoliation properties of compositions comprising hatching enzymes and eggshell polypeptides are contemplated.

The invention thus provides a cosmetic or non-cosmetic method of exfoliating and/or moisturizing skin of an animal, wherein a cosmetic or pharmaceutical composition as described hereinbefore is administered to said animal.

Thus, with reference to the above, the present invention provides a cosmetic or non-cosmetic method of exfoliating and/or moisturizing skin of an animal, wherein a cosmetic or pharmaceutical composition is administered to said animal, wherein said composition is obtained or obtainable by the method described herein.

As referred to herein, "exfoliating" refers to removing superficial cells of an epithelium surface which in skin equates to scaling or desquamation of the horny layer of the epidermis. "Moisturizing" as referred to herein covers moisturizers which prevent loss of water from the skin as well as moisturizers (humectants) that attract and retain water when applied to the skin and emollients (which improve defective desquamation).

Alternatively stated, the present invention provides a cosmetic or pharmaceutical composition as described herein for use in exfoliating and/or moisturizing skin of an animal. (The composition may alternatively be used to prepare a medicament for that purpose.)

As mentioned above, such exfoliating and/or moisturizing properties are advantageous for treating or preventing a variety of skin abnormalities, disorders or conditions.

In a preferred aspect, the skin abnormality, condition or disorder to be treated or prevented is dry skin. This may be treated by moisturizing and/or exfoliation.

"Dry skin" as referred to herein refers to an epidermis that lacks moisture or sebum, often characterized by a pattern of fine lines, scaling, and itching. Dry skin can occur as a skin condition in itself (e.g. due to age, heat/cold/dry damage) or may be the symptom of a skin disorder or condition such as sun-damage, eczema, contact dermatitis, psoriasis or ichthyosis (an inherited condition causing marked flaking of the skin).

In a further preferred aspect, the abnormality, condition or disorder to be treated or prevented is thickened horny layers of the skin. This may be treated by moisturizing and/or exfoliation.

Such thickened horny layers of the skin may occur in conditions such as calluses or corns which are protective pads made up of the thickened upper layer of skin due to repeated rubbing of the area or warts on the skin. Such methods may also be used to treat or prevent acne which involves keratinisation in its pathology. The thickened horny layers of the skin may be the condition itself or may be a symptom of a skin condition or disorder.

In a further preferred aspect, the abnormality, condition or disorder to be treated or prevented is a pigmentation disorder or abnormality of the skin. This may be treated by exfoliation.

Pigmentation disorders or abnormalities of the skin may occur as a result of age, hormonal changes, genetic factors, disease or sun or other damage. Altered pigmentation may result from a local excess of melanocytes or increases in melanocyte activity, or both. Pigmentation disorders include liver, sun or age spots (solar lentigo) and other blemishes such as freckles.

Alternatively stated, the present invention thus provides a cosmetic or non-cosmetic method of treating or preventing a condition or disorder of the skin of an animal wherein said skin is abnormally dry, the horny layer of the skin is abnormally thickened or the skin has a pigmentation disorder, wherein a cosmetic or pharmaceutical composition as described hereinbefore is administered to said animal. Said conditions or disorders are preferably as described hereinbefore.

As referred to herein "abnormal" is determined relative to normal optimum skin, i.e. healthy, hydrated, normally pigmented and non-aged skin.

In a further alternative statement, the invention provides a cosmetic or pharmaceutical composition as described herein for use in a cosmetic or non-cosmetic method of treating or preventing a condition or disorder of the skin of an animal wherein said skin is abnormally dry, the horny layer of the skin is abnormally thickened or the skin has a pigmentation disorder. (The compound or composition may alternatively be used to prepare a medicament for that purpose.)

The compositions of the invention have been found to be particularly useful in reducing skin pore size. In this respect, acne occurs in part when there is a build up of dead skin cells in the pores (hyper-keratinization of the sebaceous canal). It has been found that the compositions of the invention help to normalize the shedding of the skin cells inside the pores and prevent the clogging that, along with oil and bacteria, can produce skin lesions, e.g. inflamed lesions, such as papules and pustules and non-inflamed lesions, such as blackheads and whiteheads. Hence, the compositions defined herein may be used in a cosmetic or non-cosmetic method of reducing skin pore size.

Alternatively viewed the compositions of the invention may be used in a cosmetic or non-cosmetic method of treating or preventing acne, e.g. inflamed and/or non-inflamed skin lesions, such as papules, pustules, blackheads and/or whiteheads. (The compound or composition may alternatively be used to prepare a medicament for that purpose.)

In a preferred aspect the medical and/or cosmetic uses are achieved by topical administration to the skin.

Thus in a particularly preferred aspect, the cosmetic or pharmaceutical compositions defined herein may be used for treating disorders in which the skin is abnormally dry, the horny layer of the skin is abnormally thickened or in which a pigmentation defect is present, e.g. calluses, corns, warts, eczema, contact dermatitis, psoriasis, ichthyosis, acne and liver spots.

In a further particularly preferred aspect, the cosmetic or pharmaceutical compositions defined herein may be used for treating disorders in which the skin is abnormally dry.

As used herein, "treating" refers to the reduction, alleviation or elimination, preferably to normal levels, of one or more of the symptoms or effects of said condition or disorder e.g. presence or extent of dry or thickened skin, extent or area of pigmentation, itching or pain etc. relative to the symptoms or effects present on a different part of the body of said individual where the skin does not suffer from said condition or disorder and not subject to said treatment or in a corresponding normal individual not subject to said treatment.

"Preventing" refers to absolute prevention, or reduction or alleviation of the extent or timing (e.g. delaying) of the onset of that symptom or effect. For example conditions typified by dry, thickened or abnormally pigmented skin may be prevented by regular application of compositions of the invention before the appearance of such a condition.

The method of treatment or prevention according to the invention may advantageously be combined with administration of one or more active ingredients which are effective in treating or preventing the disorders or conditions and/or to achieve moisturization or exfoliation. Thus, cosmetic or pharmaceutical compositions of the invention may additionally contain one or more of such active ingredients.

According to a yet further aspect of the invention we provide cosmetic or pharmaceutical compositions as herein defined and optionally one or more additional active ingredients as a combined preparation for simultaneous, separate or sequential use in human or animal therapy, preferably as described herein.

The compositions of the invention may be formulated in a conventional manner with one or more physiologically acceptable carriers, excipients and/or diluents, according to techniques well known in the art using readily available ingredients.

The compositions described herein may be formulated in a conventional manner with one or more physiologically acceptable carriers, excipients and/or diluents, according to techniques well known in the art using readily available ingredients. The compositions may be provided as water based, glycerin based, alcohol (up to 20%) based, acrylate based oil/water emulsions, xanthan gum based oil/water emulsions or water/oil emulsions, for example, at pH 3.5-11, preferably pH 5.5-9.

Thus, the compositions may be incorporated, optionally together with other active substances as a combined preparation, with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme. Such compositions form compositions of the invention (i.e. are prepared in accordance with step (g)).

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like. Some of these components are described in more detail below.

Other active ingredients or components in the cosmetic or pharmaceutical composition may be selected from any one or more of minerals, vitamins, enzymes, proteins, peptides, amino acids, lipids, polysaccharides, substances suitable as sunscreen filters, chemical exfoliants, extracts, skin-conditioning agents, antioxidants and mixtures thereof.

Examples of additional proteins that may be included in the composition of the invention include collagen and/or a derivative thereof (e.g. portions thereof as defined above), a protein or peptide which is capable of promoting cell growth, glycoprotein 1, glycoprotein 2 and laminin.

The composition of the invention may be provided with enzymes including, but not limited to, any one or more of, fruit enzymes (e.g. bromelain), superoxide dismutase, peroxidase, hyaluronidase and mucopolysaccharidase.

Peptides may be selected from, but are not limited to, any one or more of D,L-carnosine, D-carnosine, L-carnosine, anserine and Matrixyl (pentapetide derivative).

Amino acids may be selected from, but are not limited to, any one or more of L-alanine, L-arginine, L-asparagine, L-aspartic acid, L-cysteine, L-cystine, glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine, and L-valine and derivatives thereof including non-naturally occurring amino acids as defined in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine |  | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |

TABLE 1-continued

| Non-conventional amino acid | Code | Non-conventional amino acid | Code |
|---|---|---|---|
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-a-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhser |

Particularly preferred amino acids as antioxidants may be selected from any one or more of glycine, lysine, arginine, cysteine, cystine, histidine, tyrosine and tryptophan.

The composition of the invention may comprise one or more lipids which includes fats, oils, waxes and the like. Suitable polar oils are, for example, those from the group of lecithins and fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, olive oil, sunflower oil, soya oil, peanut oil, rapeseed oil, almond oil, palm oil, coconut oil, castor oil, wheat germ oil, grape seed oil, thistle oil, evening primrose oil, macadamia nut oil and the like.

Alternatively or additionally the oil may be selected from volatile oils, non-volatile oils or mixtures thereof. Non-volatile oils include oils that fulfil at least one of the following definitions: (a) the oil exhibits a vapour pressure of no more than 0.2 mm Hg at 25° C. and one atmosphere pressure; (b) the oil has a boiling point at one atmosphere of at least 300° C. Volatile oils include materials that are not "non-volatile" as defined above.

Non-volatile oils may be selected from non-volatile silicone oils, non-volatile hydrocarbon oils and mixtures thereof. Suitable non-volatile silicone oils include linear polymethylsiloxanes and, preferably, non-volatile silicone oils are high molecular weight dimethicones. Examples of commercially available linear polymethylsiloxanes include DC 200 Fluid 20 Cst, DC 200 Fluid 100 Cst, DC 200 Fluid 350 Cst from Dow Corning Corporation.

Suitable non-volatile hydrocarbon oils include branched esters of diglycerin or triglycerin or the esters or 1,2,3,4 butane triol or erythritol, di erythritol or tri erythyritol.

Preferably, non-volatile hydrocarbon oils comprise erythrityl triethylhexanoate (available as Salacos E-38 from Nisshin Oilio) and Polyglyceryl-2 triisostearate (available as Cosmol 43V from Nisshin Oilio), diethyl hexyl carbonate (available as Tegosoft DEC from Degussa), dicapryl Ether (available as Cetiol OE from Cognis AG), dicapryl Carbonate (available as Cetiol CC from Cognis AG), isononyl isononanoate (available as Lanol 99 from Seppic), tridecyl Neopentanoate (supplied as Ceraphyl 55 from International Speciality Products), or a mixture thereof.

Volatile oils may be selected from volatile silicone oils, both functionalized and non-functionalized, volatile hydrocarbon oils and mixtures thereof. Volatile oil useful in the present invention may be saturated or unsaturated, have a straight or branched chain or a cyclic structure or have any one or more of these features.

Examples of volatile hydrocarbons oils include polydecanes such as isododecane and isodecane (e.g., Permethyl-99A which is available from Presperse Inc.) and the C7-C15 isoparaffins (such as the Isopar Series available from Exxon Chemicals).

The volatile silicone oil may be selected from cyclopentasiloxane, cyclohexasiloxane or a mixture thereof. Examples of commercially available volatile cyclic silicone oils include DC 244, DC 245, DC 344, and DC 345 from Dow Corning Corp.; SF-1204 and SF-1202 Silicone Fluids from Momentive Performance Materials; GE 7207 and 7158 from General Electric Co.); and, SWS-03314 from SWS Silicones Corp.

The linear volatile silicone oil may be a linear polymethylsiloxane. An example of commercially available linear polymethylsiloxanes include DC 200 Fluid, 5 Cst from Dow Corning Corp.

The composition of the invention may further comprise one or more polysaccharides selected from, but not limited to, any one or more of anionic polysaccharides (e.g. alginic acid, pectin, xanthan gum, hyaluronic acid, chondroitin sulfate, gum arabic, gum karaya, gum tragacanth, carboxymethyl-chitin, cellulose gum, glycosaminoglycans), cationic polysaccharides (e.g. chitosan, acetylated chitosan, cationic guar gum, cationic hydroxyethylcellulose (HEC)), nonionic polysaccharides (e.g. starch, dextrins, guar gum, cellulose ethers such as hydroxyethylcellulose, methylcellulose and nitrocellulose), amphoteric polysaccharides (e.g. carboxymethylchitosan, N-hydroxy-dicarboxyethyl-chitosan, modified potato starch) and hydrophobic polysaccharides (e.g. cetyl hydroxyethylcellulose, polyquaternium24).

The composition may further comprise a substance suitable as a sunscreen filter such as an organic sunscreen, e.g. a cinnamic derivative. The organic sunscreen active may be selected from hydrophilic organic sunscreen, hydrophobic organic sunscreen, or mixtures thereof. Suitable examples of sunscreens may be found in the CTFA International Cosmetic Ingredient Dictionary and Handbook, 7th edition volume 2, pp. 1672, edited by Wenning and Mc Ewen (The Cosmetic, Toiletry, and Fragrance Association, Inc., Washington, D.C. 1997).

The organic sunscreen may be selected from alkyl $\beta,\beta$-diphenylacrylate derivatives, $\alpha$-cyano $\beta,\beta$-diphenylacrylate derivatives, anthranilate derivatives, benzophenone derivatives, camphor derivatives, dibenzoylmethane derivatives, p-aminobenzoic derivatives, salicylic derivatives, triazine derivatives, or mixtures thereof. For instance the hydrophobic organic sunscreen may be selected from 4-(1,1-dimethylethyl)-4'-methoxydibenzoylmethane; 4-isopropyldibenzoylmethane; 4-(1,1-dimethylethyl)-4'-methoxydibenzoylmethane, 2-ethylhexyl-2-cyano-3,3-diphenylacrylate, or a mixture thereof.

An example of commercially available 4-(1,1-dimethylethyl)-4'-methoxydibenzoylmethane, also known as butyl methoxydibenzoylmethane or Avobenzone, includes Parsol™ 1789 from Givaudan Roure S. A. and Eusolex™ 9020 from Merck & Co., Inc. An example of commercially available 4-isoproplydibenzoylmethane, also known as isopropyldibenzoylmethane, includes Eusolex™ 8020 from Merck & Co., Inc. Examples of commercially available 2-ethylhexyl-2-cyano-3,3-diphenylacrylate, also known as Octocrylene, include Uvinul N539 SG from BASF; and Eusolex OCR from Rona/Merck.

In some embodiments the hydrophilic organic sunscreen may be 2-phenylbenzimidaole-5-sulfonic acid. An example of commercially available 2-phenylbenzimidaole-5-sulfonic acid, also known as PBSA, includes Eusolex 232 from Rona/Merck.

Suitable examples of cinnamic derivative sunscreens may be found in the CTFA International Cosmetic Ingredient Dictionary and Handbook, 7th edition volume 2, pp. 1672, edited by Wenning and Mc Ewen (The Cosmetic, Toiletry, and Fragrance Association, Inc., Washington, D.C. 1997). The cinnamic derivative may be selected from 2-ethylhexyl-p-methoxycinnamate, diethanolamine methoxycinnamate, 2-ethoxyethyl-p-methoxycinnamate, or a mixture thereof. For instance, the cinnamic derivative may be 2-ethylhexyl-p-methoxycinnamate.

The composition may contain a chemical exfoliant selected from, but not limited to, any one more of alpha hydroxy acids (AHAs), beta hydroxy acids (BHAs) or poly-hydroxy acids, such as salicylic acid, glycolic acid, citric acid and malic acid.

Extracts that may be incorporated in the composition include, but are not limited to plant extracts, which may comprise phenolic compounds such as, for example, flavonoids (e.g., glycosyl rutin, ferulic acid, caffeic acid), furfurylidene glucitol, butylated hydroxytoluene, butylated hydroxyanisole, nordihydroguaiaretic resin acid, nordi-hydroguaiaretic acid, trihydroxybutyrophenone and derivatives thereof. Particular plant extracts for use in the composition of the invention include aloe vera extract, ginseng extract and horsetail extract.

*Ginseng* extract is obtainable by extracting with a hydrophilic solvent (in particular, water, ethanol, glycol, or any mixtures thereof) the root of *Panax ginseng*. The extract contains saponins, sterols, carbohydrates, pectin, vitamins, minerals and lipids.

Horsetail extract is obtainable by extracting with a hydrophilic solvent (e.g., water, ethanol, glycol, or any mixtures thereof) the whole herb of *Equisetum arvense*. The extract contains silicates, flavinoids, saponosides, caffeic acid and ferulic acid.

The composition may further comprise a skin-conditioning agent. The skin-conditioning agent may be selected from humectants, exfoliants, emollients or mixtures thereof. Humectants includes polyhydric alcohols such as glycerine, propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerine or mixtures thereof.

Examples of antioxidants that may be provided in the composition of the invention include but are not limited to amino acids, vitamins, minerals, carotenoids, peptides, thiols, sulfoximine compounds, chelators, unsaturated fatty acids, phenolic compounds, plant extracts, stilbenes, uric acid, mannose, chlorogenic acid, imidazoles (e.g. urocanic acid), furfurylidenesorbitol, ubiquinone, ubiquinol, plastoquinone, phytosterols and derivatives thereof (e.g. salts, esters, ethers, sugars, nucleotides, nucleosides, peptides and/or lipid derivatives), some of which are described above.

Vitamins may be selected from, but are not limited to, any one or more of vitamin A and derivatives thereof (e.g. retinoid or retinol or their derivatives such as retinyl palmitate or retinyl proprionate), biotin, folic acid, calcium pantothenate, nicotinamide, pyridoxine HCl, pyridoxal HCl, riboflavin, thiamine HCl, thymidine, vitamin B12, vitamin B3 (e.g. niacinamide), vitamin B5 (e.g. panthenol), vitamin C and derivatives thereof (e.g., ascorbyl palmitate, Mg ascorbyl phosphate, ascorbyl acetate), tocopherols and derivatives (e.g. vitamin E acetate).

Minerals may be selected from, but are not limited to, any one or more salts of molybdenate (e.g. $(NH_4)OMo_7O_{24}$) aluminium (e.g. $AlCl_3$), calcium (e.g. $CaCl_2$), cobalt (e.g. $CoCl_2$), chromium (e.g. $CrK(SO_4)$), copper (e.g. $CuSO_4$), iron (e.g. $Fe(NO_3)_3$, $FeSO_4$), potassium (e.g. KCl), magnesium (e.g. $MgCl_2$), manganese (e.g. $MnCl_2$, $MnSO_4$), phosphate (e.g. $Na_2HPO_4$, $NaH_2PO_4$), carbonate (e.g. $NaHCO_3$), silicate (e.g. $Na_2SiO_3$), sodium (e.g. NaCl), vanadate (e.g. $NH_4VO_3$), nickel (e.g. $NiCl_2$), tin (e.g. $SnCl_2$), zinc (e.g., ZnO, $ZnSO_4$), selenium (e.g. selenomethionine, ebselen, $H_2SeO_3$, $Na_2SeO_3$), sulphate and nitrate.

Carotenoids, may be selected from, but are not limited to, any one or more of carotenes, e.g. α-carotene, β-carotene, ψ-lycopene, phytoene etc. and derivatives thereof.

Thiols may be selected from, but are not limited to, any one or more of aurothioglucose, propylthiouracil, thioredoxin, lipoic acid, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters and the salts thereof, dilauryl thiodipropionate, distearyl thiodipropionate, thiodipropionic acid and derivatives thereof.

Sulfoximine compounds may be selected from, but are not limited to, any one or more of homocysteine sulfoximine, buthionine sulfones, penta-, hexa-, heptathionine sulfoximine, which may be included in the composition such that they are provided in very low dosages (e.g. pmol to μmol/kg).

Chelators may be selected from, but are not limited to, any one or more of apoferritin, desferral, lactoferrin, α-hydroxy fatty acids, palmitic acid, phytic acid, α-hydroxy acids (e.g. citric acid, lactic acid, malic acid), humic acid, bile acid, bile extracts, bilirubin, biliverdin, EDTA, EGTA and derivatives thereof.

Unsaturated fatty acids may be selected from, but are not limited to, any one or more of γ-linolenic acid, linoleic acid, oleic acid and derivatives thereof.

Stilbenes and derivatives thereof include, for example, stilbene oxide and trans-stilbene oxide.

A variety of additional optional active ingredients may be incorporated into the compositions of the present invention. Non-limiting examples of these additional ingredients include additional skin care actives such as farnesol, bisabolol, phytantriol, urea, guanidine (e.g. amino guanidine); hexaminidine compounds, salts or derivatives thereof; sugar amines; self-tanning agents (e.g. dehydroxyacetone); structuring agents; hydrophilic gelling agents; anti-acne medicaments (resorcinol, salicylic acid, and the like); skin soothing and healing agents such as allantoin and the like; and agents suitable for aesthetic purposes such as essential oils, fragrances, skin sensates, opacifiers, aromatic compounds (e.g. clove oil, menthol, camphor, eucalyptus oil, and eugenol).

The compositions described herein may be formulated so as to provide quick, sustained or delayed release of the active ingredients after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

The use of solutions, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

The emulsifier may be selected from nonionic emulsifiers, anionic emulsifiers, cationic emulsifiers, zwitterionic emulsifiers, amphoteric emulsifiers or mixtures thereof. Emulsifiers are known in the art. See, e.g., McCutcheon's, Detergents and Emulsifiers, North American Edition (1986), published by Allured Publishing Corporation.

When the cosmetically or pharmaceutically acceptable carrier is a water-in-silicone emulsion, emulsifiers are preferably selected from polyoxyalkylene copolymers, polyglyceryl copolymers or mixtures thereof. Polyoxyalkylene copolymers, also known as silicone polyethers, are described in detail in U.S. Pat. No. 4,268,499. An example of commercially available polyoxyalkylene copolymers includes DC5225C or DC2-5185C (PEG/PPG-18/18 dimethicone available as blend with cyclopentasiloxane) from Dow Corning Corp.; and, KF6017 or KF6028 (PEG-9 dimethicone) from Shin-Etsu Inc. Examples of commercially available polyglyceryl emulsifiers include KF6100 and KF6104 from Shin-Etsu Inc.

Compositions are preferably for topical (i.e. to the skin) administration.

Topical compositions include gels, creams, ointments, sprays, lotions, salves, sticks, soaps, powders, films, aerosols, drops, foams, solutions, emulsions, suspensions, dispersions e.g. non-ionic vesicle dispersions, milks and any other conventional cosmetic or pharmaceutical forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

In some embodiments the compositions described herein may be topically administered to the skin via a product, device or material to which the polypeptide or composition has been applied, impregnated or chemically bonded. To this end, bandages, plasters (e.g. adhesive patches), gauze, surgical tape, cotton swabs or other absorbent materials, e.g. a puff, fleece, or sponge, or supportive matrices may be coated, impregnated or chemically bonded with a composition as described herein. For example, many compositions can be applied to the skin using dermal patches that are well described in the art, e.g. US 2008/0038300, US 2009/

0043236, WO 2005/067499 and WO 2009/085302, which are incorporated herein by reference. In some embodiments, the material comprising the composition as described herein may be in the form of a device that can be, e.g. worn by the subject to be treated. For instance, the composition as described herein may be applied, impregnated or chemically bonded onto a material or supportive matrix that forms all or part of a diaper, glove, sock etc.

Hence, a further aspect of the invention comprises the provision of a product, material or device which is coated, impregnated or chemically bonded with a composition as described herein. The invention also extends to such products, materials or devices for uses as described herein. Preferably said product is a bandage, plaster (e.g. adhesive patch), gauze, surgical tape or cotton swab or said device is a diaper, glove or sock.

The cosmetic or pharmaceutical compositions can be included in a container, pack, or dispenser together with instructions for administration.

In some embodiments, the compositions may be provided in a form adapted for oral or parenteral administration. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

The concentration of the active ingredients in compositions described herein, may depend upon the source of the composition (i.e. the starting material for the method described above), the mode of administration, the course of treatment, the age and weight of the patient, the cosmetic or therapeutic indication, the body or body area to be treated and may be varied or adjusted according to choice. Generally however, the composition prepared according to the method of the invention after filtration step (f) is diluted in step (g) to 0.001, 0.005, 0.01 or 0.1 to 50%, e.g. 0.005-40%, e.g. 0.1 to 25%, such as 0.1 or 0.5 to 5, e.g. 1-5% (w/w or v/v) to provide the final preparation for administration, particularly for topical administration, e.g. a 1% or 3% solution of the composition after step (f).

When additional components are added to the composition made by the above described method, e.g. additional moisturizing agents as described herein, the additional component may be present in the amounts 0.0001, 0.0005, 0.001 or 0.01 to 50%, e.g. 0.0005-40%, e.g. 0.01 to 25%, such as 0.1 or 0.5 to 5, e.g. 1-5% (w/w of the final preparation for administration, particularly for topical administration). Effective single doses for the composition may lie in the range of from 0.0001-100 mg/cm$^2$/day (total protein in the composition), e.g. 0.1-100 mg/cm$^2$/day, preferably 0.0001-10 mg/cm$^2$/day, e.g. 0.1-10 mg/cm$^2$/day, when applied topically, depending on the mammalian animal being treated, taken as a single dose.

The administration may be by any suitable method known in the medicinal arts, including for example oral, intestinal, percutaneous, buccal, rectal or topical administration or administration by inhalation. The preferred administration forms will be administered orally, or most preferably topically. As will be appreciated oral administration has its limitations if the active ingredient is digestible. To overcome such problems, ingredients may be stabilized as mentioned previously.

Preferably liquid solutions, creams or suspensions would be employed for topical administration.

Animals to which the compositions may be applied or administered are limited to mammals. Preferably the mammals are primates, domestic animals, livestock and laboratory animals. Thus preferred mammalian animals include mice, rats, rabbits, guinea pigs, cats, dogs, monkeys, pigs, cows, goats, sheep and horses. Especially preferably the compositions are applied, or administered, to humans.

The following Examples are given by way of illustration only in which the Figures referred to are as follows.

Figure 4:
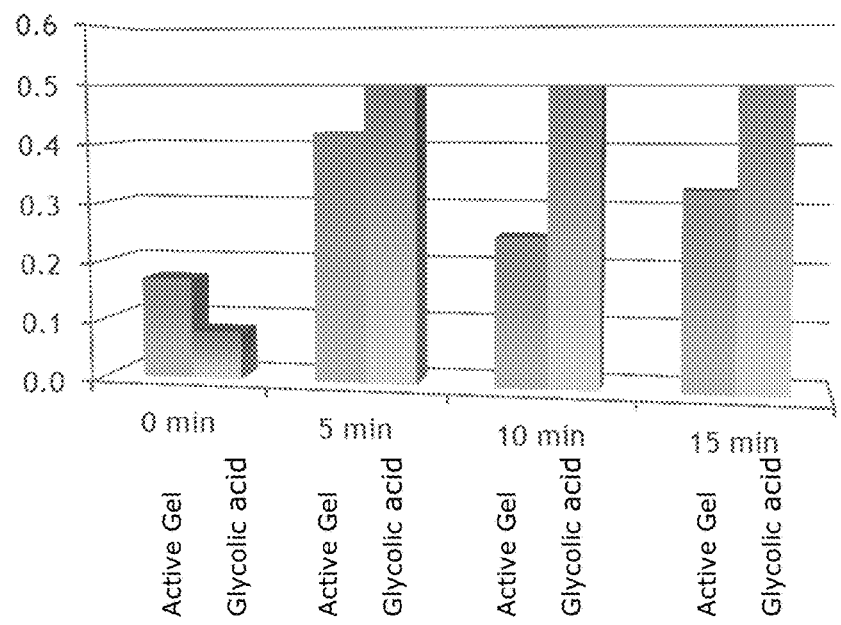
Figure 4:
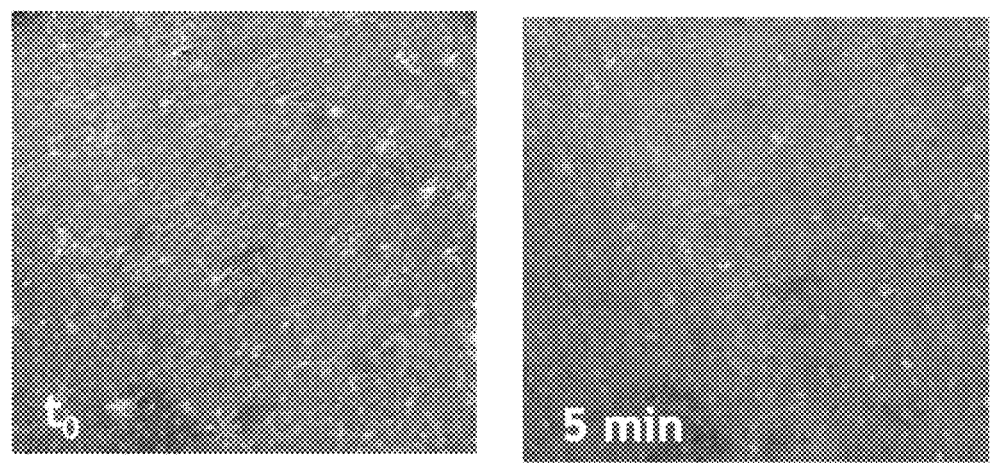

FIG. 4 shows a bar chart (A) comparing the exfoliation effect of a gel (Active Gel) comprising 3% of the hatching fluid composition prepared in step (f) in the method of the invention and a 3% solution of glycolic acid using a D-Squame test. A lower score indicates less scaliness, i.e. increased exfoliation. (B) shows a photograph of the test area treated with the active gel at t0 and after 5 minutes.

Figure 5:
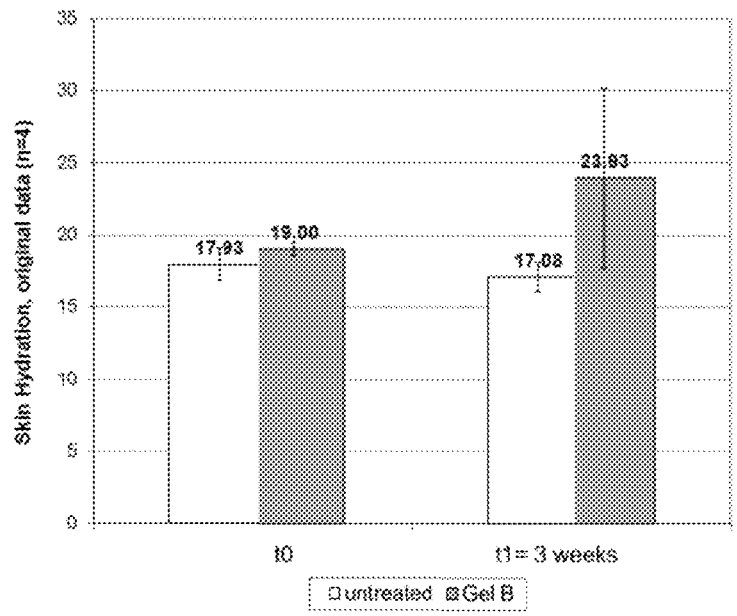
Figure 5:
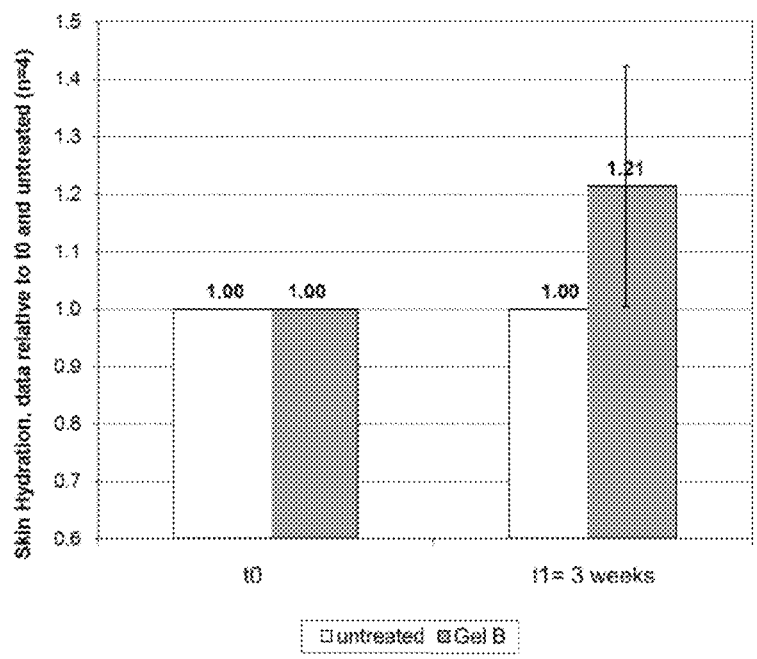

FIG. 5 shows bar charts depicting (A) the mean increase and (B) the relative increase in skin hydration compared to untreated skin after 3 weeks of a twice daily treatment with a gel (Gel B) comprising 3% of the hatching fluid composition prepared in step (f) in the method of the invention.

Figure 6:
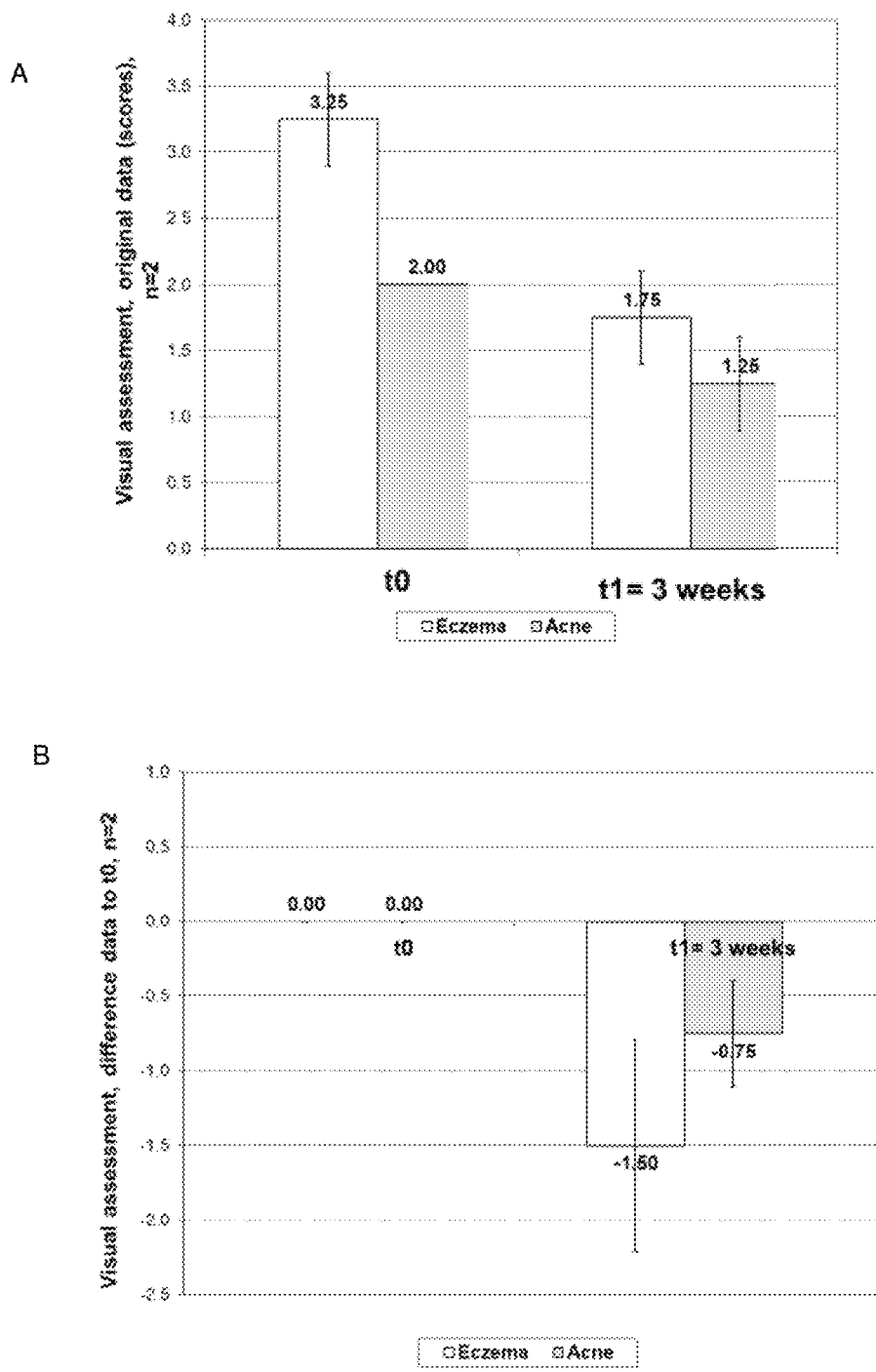

FIG. 6 shows bar charts depicting (A) the mean visual assessment and (B) the relative visual assessment of the severity of the eczema or acne compared to untreated skin after 3 weeks of a twice daily treatment with a gel comprising 3% of the hatching composition prepared in step (f) in the method of the invention.

Figure 7:
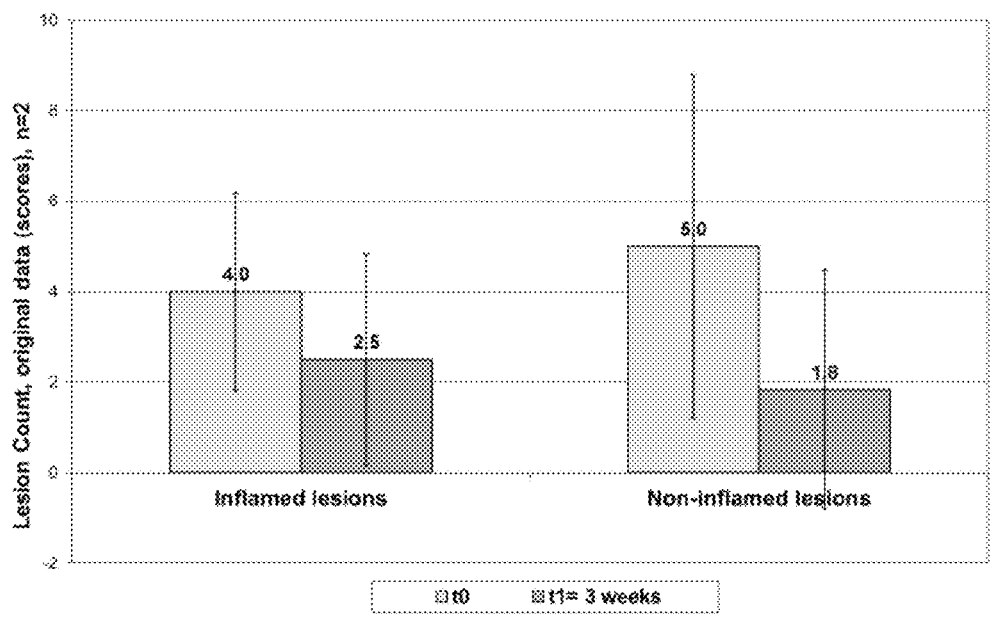
Figure 7:
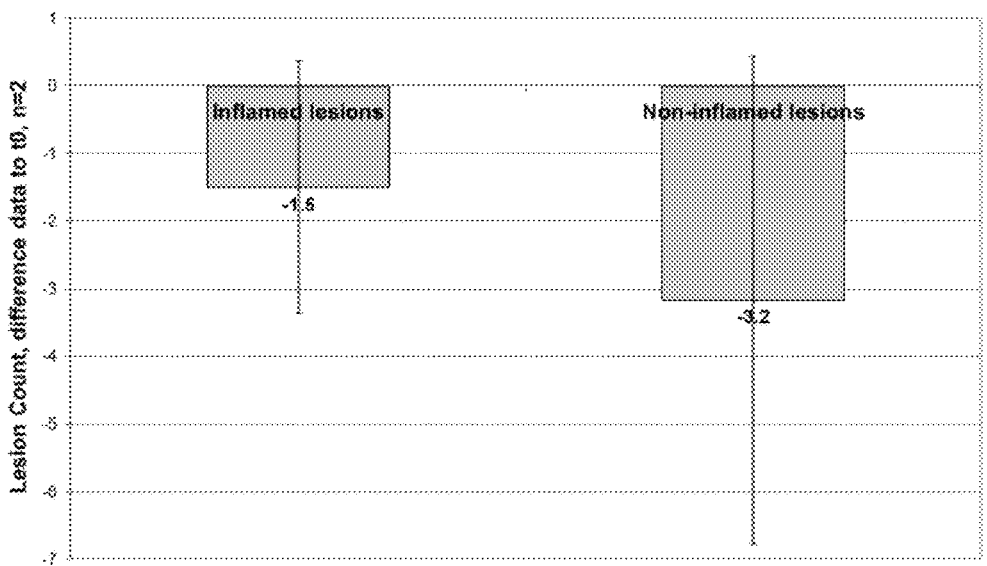

FIG. 7 shows bar charts depicting (A) the mean decrease and (B) the relative decrease in the number of inflamed and non-inflamed skin lesions compared to untreated skin after 3 weeks of a twice daily treatment with a gel comprising 3% of the hatching composition prepared in step (f) in the method of the invention.

EXAMPLES

Example 1: Preparation of the Composition

The composition was prepared from salmon hatching fluid. To improve the protein concentration of hatching fluid, salmon eggs were transferred to minimal volumes of water prior to hatching. Highly synchronous hatching can be induced by elevated (room) temperatures, or by deoxygenation (Oppen-Berntsen et al. 1990, Aquaculture, 86, pp. 417-430), which yields a small volume of highly concentrated preparation of crude polypeptides and portions of polypeptides. Hatching should be complete within 2 hours for more than 95% of the embryos.

The hatching fluid was filtered using a standard filter with a 7 μm pore size, to remove material likely to clog filters in subsequent filtration steps. This filtrate, the processed hatching fluid, may be frozen for years without significant degradation, before being thawed and employed for further protein purification. This fact greatly simplifies production of a starting material for preparing the hatching fluid composition.

The processed hatching fluid was loaded on to a diethylaminoethyl (DEAE) ion exchange column according to the manufacturer's instructions and washed with a solution of 20 mM Tris HCl (pH 8.50). The flowthrough was discarded. Leukolectin proteins were eluted from the column with the wash solution containing 50 mM NaCl. The eluate was collected for other uses. The polypeptides of interest (i.e. metalloproteinase, serine protease and eggshell polypeptides) were eluted from the column with the wash solution containing 1M NaCl. The eluate was collected and then diafiltrated with a filter exclusion size of 8 kDa to exchange the water of the hatching fluid for buffer. In this case, the buffer was phosphate buffered saline, although other buffers are equally suitable. For example, buffer containing 0.5 mM phosphate and 1 mM NaCl or buffers containing millimolar Tris (e.g. 10 mM) at pH around neutrality or slightly alkaline (pH 7.5-8.5), containing 5 mM NaCl, are suitable. The retentate from the diafiltration step was collected and diluted by the addition of the buffer.

Finally, the filtrate was subjected to filtration through a filter with a pore size of 0.22 μm and the final filtrate was collected. This filtrate is a highly enriched preparation of the metalloproteinase, serine protease and eggshell polypeptides and portions of polypeptides found in the crude hatching fluid, comprising no or only trace amounts of leukolectin polypeptides from the hatching fluid.

Example 2: In Vivo Effects of the Composition on Skin Pore Size

The hatching fluid composition was prepared as described in Example 1. The composition was prepared as a 1% gel [v/v] (total volume of composition per unit volume of gel) and compared to a control gel which did not comprise the active component, i.e. the hatching fluid composition (Gel B in FIG. 1). The gel comprised a preservative (0.8%), diglycerin (3.00%) and xanthum gum (0.8%), in water.

A double blind, placebo controlled clinical trial was conducted on 23 female voluntary subjects. The 23 subjects were of ages between 22.4 and 58.7 years (39.3±13.6 years).

The trial used a split-face design. The application sites were the right or the left half of the face. The active gel was allocated to the test sites as randomized (right/left). The pore size analysis was performed on pores on the cheek area above the nasolabial fold.

The active gel was applied twice a day by the subjects at home over a period of 4 weeks. The gel was applied at a quantity of usual practise to half of the face, with the other half left untreated (allocation as randomised).

To visualize the pore size, a zinc-oxide-containing cream (Penaten®) was applied to the measurement area so that the cream was incorporated into the pores. The surplus was carefully removed with a tissue. Micro images were taken by a Canon PowerShot G9 digital camera using the D-scope II attachment (lens with 40× magnification) and recorded by the FotoFinder® 2007 mediscope software. The D-Scope has a prism reflector ring and integrated LED lamps, guaranteeing balanced illumination of the viewing area. One image per test site was taken. After completion of the study, the software ImageJ was used to measure the size (diameter) of three selected pores per test site. The same pores were measured at t0 and t1.

Images for the pore size analysis were taken before starting the first gel application (t0) and after 4 weeks of treatment (t1). All assessments were performed in a climate controlled room at 21.5° C. (±1° C.) and 50% (±5%) relative humidity. The assessment at point in time t1 occurred 10-20 hours after the last product treatment.

For evaluation of the differences between the test sites at t0, the original data were analyzed. For evaluation of the differences between the test sites after treatment (t1), the data relative to t0 and the untreated situation were analyzed. The double relative data (data relative to t0 and the untreated situation) were computed as follows: (treatment situation at t1/treatment situation at t0)/(untreated situation at t1/untreated situation at t0). These data reflect the change in the parameters taking account of the alterations of the untreated situation (control) and of differences between the test sites before they were subjected to different treatments (including the control test site).

Results

The t0 situation was homogenous. The test site that was to be treated with the active gel after the t0 assessment did not significantly differ in pore size from the test site that was to be left untreated (p=0.3811). At t0, the pore size was on average 0.60(±0.19) mm for the untreated test site and 0.65(±0.22) mm for the active gel treated test site.

Figure 1:
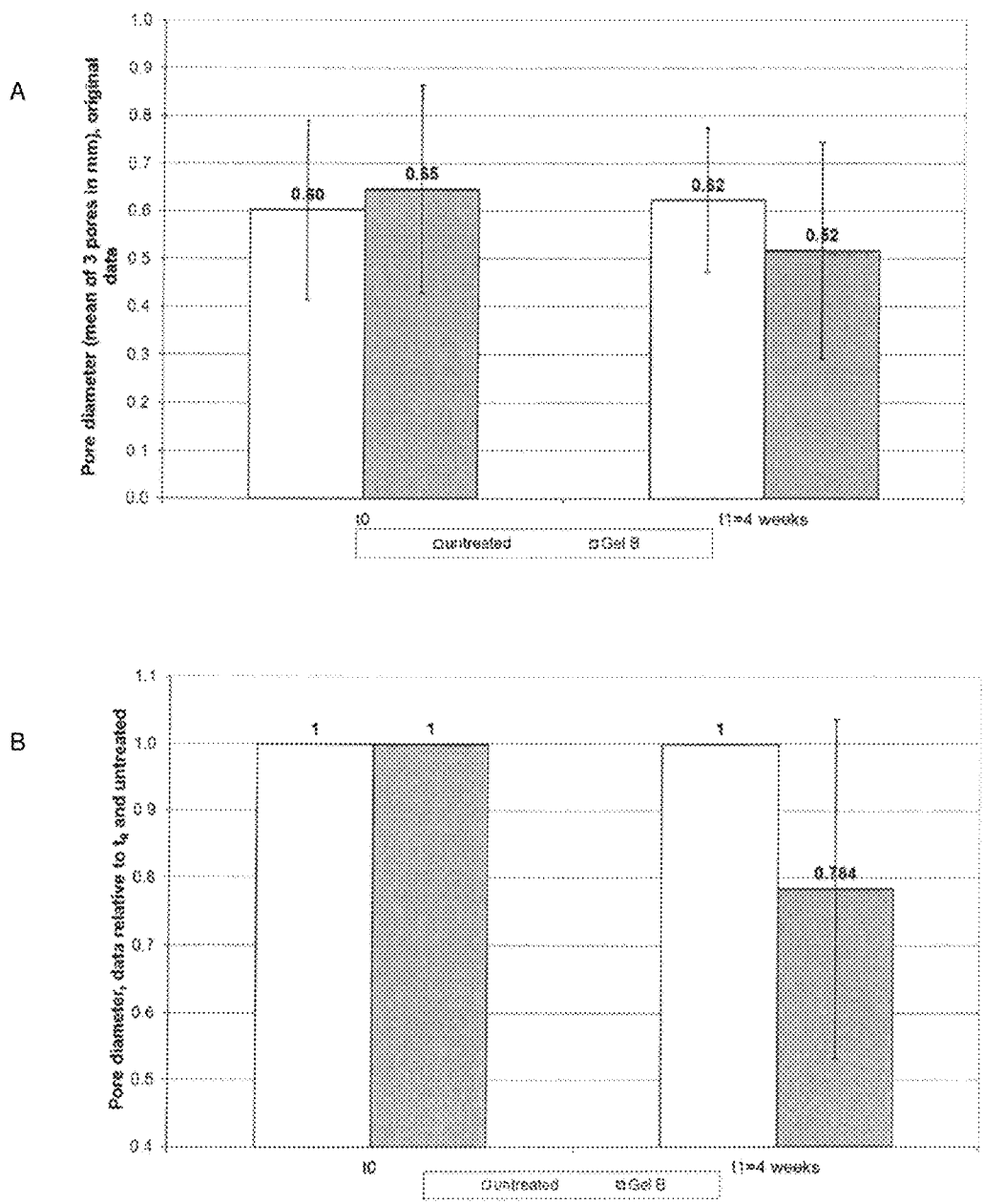
FIG. 1 shows bar charts depicting (A) the mean decrease and (B) the relative decrease in skin pore diameter compared to untreated skin after 4 weeks of a twice daily treatment with a gel (Gel B) comprising 1% of the hatching fluid composition prepared in step (f) in the method of the invention.

The pore size of the untreated test site was homogeneous within the study period (p=0.5084). Concerning the data relative to t0 and untreated t1, the skin treated with the active gel (i.e. comprising 1% of the hatching fluid composition of step (f)) showed a statistically significant decrease in the pore size by about 22% compared to the untreated situation after four weeks of daily treatment (p=0.0005) (FIG. 1). There was no adverse skin reaction recorded.

Example 3: In Vivo Effects of the Composition on Skin Lesions (Acne)

Figure 2:
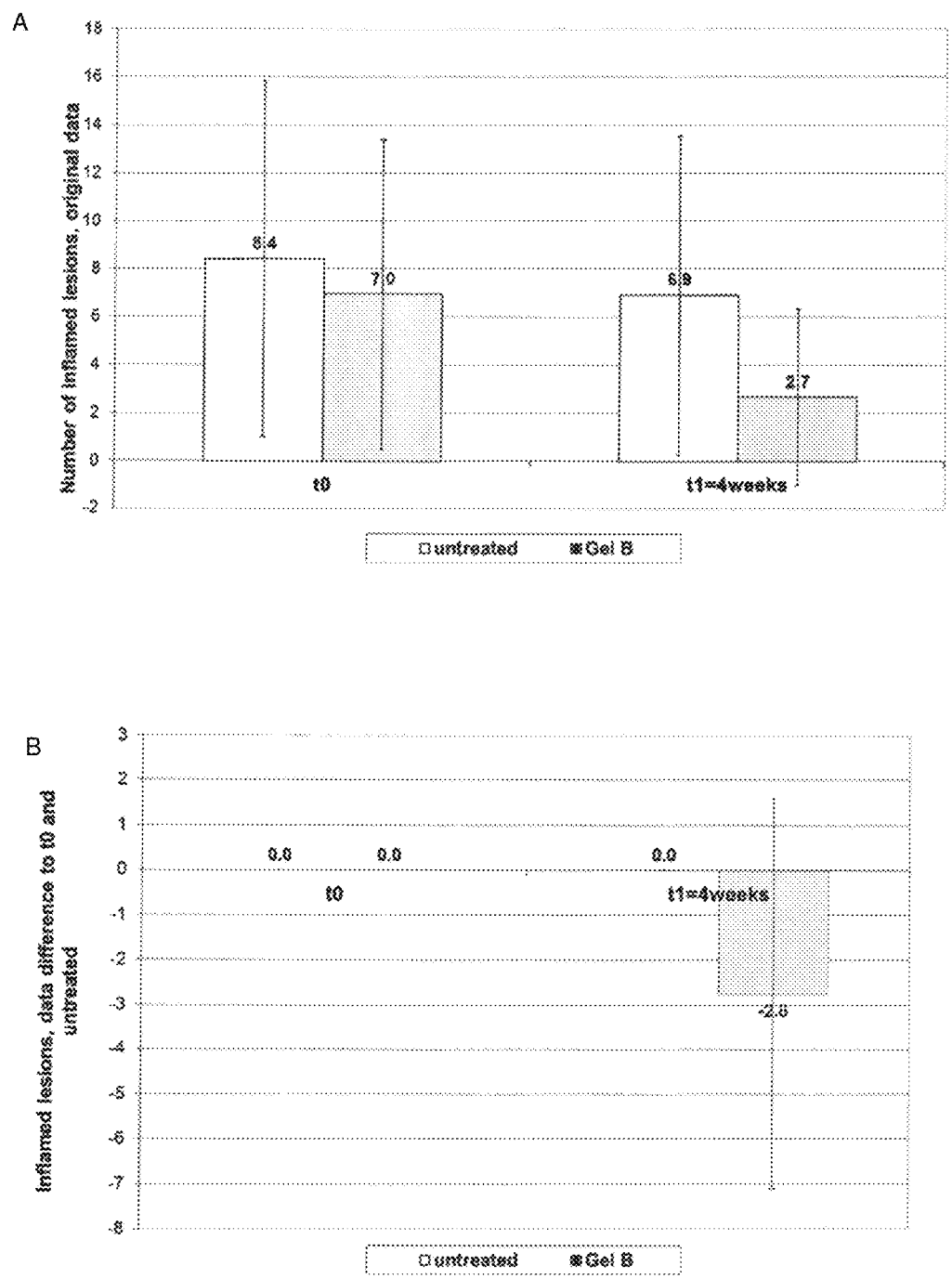
FIG. 2 shows bar charts depicting (A) the mean decrease and (B) the relative decrease in the number of inflamed skin lesions compared to untreated skin after 4 weeks of a twice daily treatment with a gel (Gel B) comprising 1% of the hatching fluid composition prepared in step (f) in the method of the invention.

A gel comprising the hatching fluid composition of step (f) was prepared as described in Example 2 (Gel B in FIG. 2).

A double blind, placebo controlled clinical trial was conducted on 21 qualified female voluntary subjects. The subjects were of ages between 18.2 and 34.5 years (26.3±5.0 years). The subjects were qualified to participate in the study by having spots on their forehead, cheeks and/or chin.

The trial used a split-face design. The application sites were the right or the left half of the face including forehead, cheeks and chin. The active gel was allocated to the test sites as randomized (right/left).

The active gel was applied twice a day by the subjects at home over a period of 4 weeks. The product was applied at a quantity of usual practise to half of the face, with the other half left untreated (allocation as randomised).

The number of inflamed (papules, pustules) and non-inflamed (blackheads, whiteheads) lesions were visually counted on both test sites before starting the first gel application (t0) and after 4 weeks of treatment (t1). All assessments were performed in a climate controlled room at 21.5° C. (±1° C.) and 50% (±5%) relative humidity. The assessment at point in time t1 occurred 10-20 hours after the last product treatment.

The lesion count was performed by the same assessor at both assessments for any given subject. All lesion counts were performed under standard lighting conditions. Counts were made on the forehead, cheeks and chin (but not the nose area) for each of blackheads (open comedones), whiteheads (closed comedones), papules and pustules.

Results

Inflamed Lesion Counts

The t0 situation was not homogenous. The test site that was to be treated with the active gel after the baseline assessment differed significantly in the number of inflamed lesions from the test site that was to be left untreated (p=0.0217). At t0, the number of inflamed lesions was on average 8.4(±7.4) for the untreated test site and 7.0(±6.5) for the active gel treated test site. The number of inflamed lesions of the untreated test site was homogeneous within the study period (p=0.0815).

The skin treated with the active gel showed a statistically significant decrease in the number of inflamed lesions compared to the untreated situation after four weeks of daily treatment (p=0.0086) (FIG. 2). There was no adverse skin reaction recorded.

Non-Inflamed Lesion Counts

The t0 situation was homogenous. The test site that was to be treated with the active gel after the baseline assessment did not significantly differ in the number of non-inflamed lesions from the test site that was to be left untreated (p=0.8753). At t0, the number of non-inflamed lesions was on average 3.2(±5.3) for the untreated test site and 2.8(±3.2) for the Gel B treated test site. The number of non-inflamed lesions of the untreated test site was homogeneous within the study period (p=0.9057).

Figure 3:
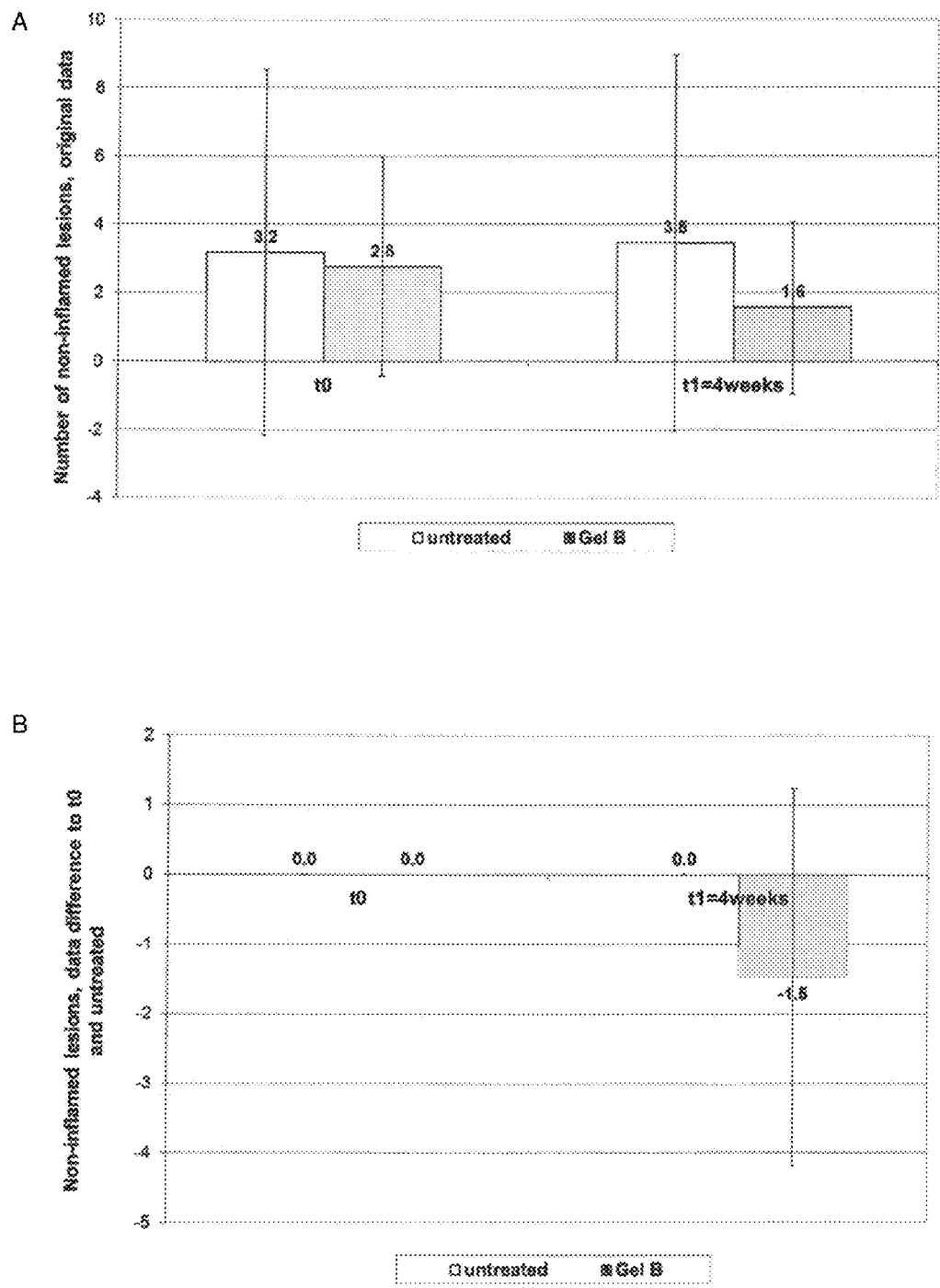
FIG. 3 shows bar charts depicting (A) the mean decrease and (B) the relative decrease in the number of non-inflamed skin lesions compared to untreated skin after 4 weeks of a twice daily treatment with a gel (Gel B) comprising 1% of the hatching fluid composition prepared in step (f) in the method of the invention.

The skin treated with active gel showed a statistically significant decrease in the number of non-inflamed lesions compared to the untreated situation after four weeks of daily treatment (p=0.0215) (FIG. 3). There was no adverse skin reaction recorded.

Example 4: In Vivo Effects of the Composition on Exfoliation

A gel comprising 3% of the hatching fluid composition of step (f) was prepared as described in Example 2.

A double blind, placebo controlled clinical trial was conducted on 3 female subjects with visible signs of dry and scaly skin on both calves. The 3 subjects were of ages between 38.4 and 57.8 years (on average 48.1±9.7 years).

The study was used to analyse the effect of the gel comprising the hatching fluid composition on exfoliation compared to glycolic acid (3%). There were 8 test areas on the calves, i.e. 4 on each calf for treatment with either the active gel or glycolic acid. Allocation of the product treatment to the test areas was permutated. Among the four test sites one was left untreated whereas the three others were product treated for 5 min, 10 min or 15 min.

Immediately before the test product treatment (t0), a D-Squame® sample was taken from each calf (at the overlapping area of the four test sites). The active gel and the glycolic acid (3%) were applied once by a technician onto the respective test site on the calves. The products were allowed to act on the skin for 5 min, 10 min and 15 min, with one test not treated ("0 min"). Then, all 4 test sites were rinsed-off with water and allowed to be air-dried before a D-Squame® sample was taken from all 4 test sites. All D-Squame® discs were transferred to the black storage cards and visually assessing with regard to the degree of scaliness using the following score:

Score 0: absent
Score 1: slight
Score 2: moderate
Score 3: severe
Score 4: extreme There were no discomfort adverse reactions.

Results

The assessment of exfoliation on 3 subjects using D-Squames® revealed a higher reduction in scaliness on average for the active gel compared to the glycolic acid after treatment regimens of 5 min, 10 min or 15 min (FIG. 4).

Example 5: In Vivo Effects of the Composition on Skin Hydration

A gel comprising 3% of the hatching fluid composition of step (f) was prepared as described in Example 2.

A double blind, placebo controlled clinical trial was conducted on 4 subjects. The subjects were qualified to participate in the study by having dry skin on the forearms. The 4 subjects were of ages between 56.3 and 70.9 years (on average 64.3±6.3 years).

The test sites to analyse skin hydration were both forearms. There were four test areas on the forearms, namely two on each inside of the forearm. Two areas were treated with the active gel comprising the hatching fluid composition, one was treated with glycerine (control) and the fourth was left untreated.

The treatments were performed twice a day by the subjects at home over a period of three weeks. The products were applied at a quantity of about 2 $mg/cm^2$ to the corresponding forearm test site (as randomised, with one test site left untreated and another treated with glycerine as control).

Before starting the first product application (t0) and after three weeks of treatment (t1) the skin hydration on the forearm (Corneometer CM825®, 10 repeated measurements) was measured.

All measurements were performed in a climate controlled room at 21.5° C. (±1° C.) and 50% (±5%) relative humidity after the subjects had adapted with their uncovered test areas to these indoor climate conditions for at least 30 min. The measurements and treatments at point in time t1 occurred 10-20 hours after the last product treatment.

Results

The skin treated with the active gel (gel B) comprising 3% v/v of the hatching fluid composition of step (f) showed a mean increase in skin hydration on 4 subjects of about 21% compared to the untreated situation after 3 weeks of a twice daily product treatment (FIG. 5).

Example 6: In Vivo Effects of the Composition on Eczema and Acne

A gel comprising 3% of the hatching fluid composition of step (f) was prepared as described in Example 2.

A double blind, placebo controlled clinical trial was conducted on 4 subjects, 2 for eczema and 2 for acne. The subjects were qualified to participate in the study by having eczema or acne (visually assessed by an expert). The effect of the active gel on the grade of eczema or acne was analysed on the selected problematic area, i.e. on the hand or arm (eczema) or the face (acne).

The active gel was applied twice a day in the morning and in the evening by the subjects at home over a period of three weeks, using an amount of product which corresponds to actual practice.

Immediately before starting the first product application (t0) and after three weeks of treatment (t1), the grade of eczema or acne was visually assessed by objective dermatological life scoring and subjective assessment by the subjects themselves. Lesion counts (number and quality of non-inflamed (whiteheads and blackheads) and inflamed lesions (papules and pustules) were dermatologically assessed (only for the 2 subjects with facial acne)).

The visual expert assessment and the subjective assessment were performed according to the following score:

Score 0: absent
Score 1: slight
Score 2: moderate
Score 3: severe
Score 4: extreme The visual expert assessment as well as the subjective assessment (data not shown) showed a reduction on the grade of eczema and acne in the average on 2 subjects after a 3 week treatment regimen with the active gel (FIG. 6). The lesion count revealed a reduction in the number of inflamed and non-inflamed lesions in the mean on 2 subjects after a 3 week treatment regimen with the active gel (FIG. 7).

---

Sequences:

SEQ ID No. 1: Metalloproteinase - Atlantic salmon
MDHRPTLSLL LLLLLLGLSQ ASGNEFHDEP DHVSITSVIL
KSNNGTNELL LDGDILAPRT RNAMKCFSSQ YSCLWKKSSD
GLVYVPYILS AVYSSLEVET IETAMKYFQG KTCIRFIPRK
TQTAYLDIQS SGGCFGTVGT VGDRQTLSLA QFGCVQHGII
QHELLHALGF HEHNRSDRE QYIRINWQYI YDYAVGNFQK
EDTNNLHTAY DYSSVMHYDR TAYTNDYGKE TITPIPDPSV
AIGQRLGMSD IDVLKVNKLY QC SEQ ID No. 2: Eggshell polypeptide I fragment - Atlantic salmon
TVTVQCTKDG QFVVVVSRDA TLPNLELDSI SLLGANGAHC
TPVGTTSAFA IYQFKVTECG TVVTEEPDTI VYENRMSSSY
VVGIGPFGDI TRDSHYDLVF QCRYTGTSVE TLVIEVK SEQ ID No. 3: Eggshell polypeptide II fragment - Salmon
AVTVQCTKDG QFVVVVARDA TLPSLELDSI SLLGTNGPHC
HAIGTTSVFA IYQFKVTECG TVMTEETDTI IYENRMSSSY
QVGVGPFGSI TRDSQYDLTF QCRYKGSTIV AVVIDVKPVP
PNPDIAPGP LTVELRLGSG TCLTKGCNEE EVAYTSYYTE
ADYPVTKVLR DPVYTEVRIL ARTDPNIVLT LGRCWATTNP
NPLSLPQWDL LIDGCPYQDD RYLTTPINVG PSSGLSFPTH
YRRFVLKMFT FVDPMSMTPL R SEQ ID No. 4: Eggshell polypeptide III fragment - Salmon
AECRENMVHV EAKHDLLGIG QLIQLEDLTL GDCPMSGFDN
INQVLIFESP LQSCGSQLRM TTNSLIYIFT LYYKPKPLAN
TPLIRTNDAM INIECHYPRK HNVSSLALIP TWTPFSAAKY
AEELLYFSMR LMTADWQYER AGNMYVLGDM VNIEASVMQY
FHVPLRIFVD SCVATLEPNI NANPRYAFIE NHGCLIDAKM
TGSHSQFMPR SADYKLYFQV EAFR SEQ ID No. 5: Full length zr-protein - Atlantic salmon
MKWSAVCLVA VATLGWLCDA QNFLEKPGWP PIQTPPSWPP
QTPQRPVQPL PQRPAQPFLQ KPAQPIPQRI PYTEDDTKQT
CEVVDKDKVS CGLSGITAAQ CQAISCCFDG RMCFYGKTVT
VQCTKDGQFV VVVSRDATLP NLELDSISLL GANGAHCTPV
GTTSAFAIYQ FKVTECGTVV TEEPDTIVYE NRMSSSYVVG
IGPFGDITRD SHYDLVFQCR YTGTSVETLV IEVKTYPNPN
PVVTVDAVLN VELRLANGRC LSKGCDEMQE AYTSYYTVAD
YPVTKVLRDP VYAEVRILGM TDPNVVLTLE QCWATIDPTG
DRLPRWDLLV NGCPYQDDRY LTVPIASDSS YIPPGEFLSH
YKRFVFKMFT FVDPTSMVPL QENVYIHCRA TVCHALAGSC
EQRCNRQRRD LSAQGQKKTK GDVVVSSQKV IMIDPSLYA SEQ ID No. 6: Full length choriogenin H - Pacific salmon
MKWSAVCLVA VATLGWLCDA QIYLEKPGWP PIQTPASWPA
QPPEKPVQPP QRPAQPPQWP AQPPQWPAQP PQRPAQPPQR
PAQTQQWPGQ PPQRPAQPPQ WPAQPPQRPA QPPQRPAQPP
QRPAQPPPRP AQPPQWPVHP PQWPVQPGTP LQRPKFPSDP
GSKQSCDVDS QHKVQCGLPD ITAAHCDAIN CCFDGRMCFY
GKAVTVQCTK DGQFVVVVAR DATLPSLELD SISLLGTNGP
HCHAIGTTSV FAIYQFKVTE CGTVMTEETD TIIYENRMSS
SYQVGVGPFG SITRDSQYDLTFQCRYKGST IVAVVIDVKP
VPPPNPDIAP GPLTVELRLG SGTCLTKGCN EEEVAYTSYY
TEADYPVTKV LRDPVYTEVR ILARTDPNIV LTLGRCWATT
NPNPLSLPQW DLLIDGCPYQ DDRYLTTPIN VGPSSGLSFP
THYRRFVLKM FTFVDPMSMT PLRETVFIHC NTAVCLPSHG
DSCEPRCYRK RRDIPAAVQK TTRIKSNLVS SGELILTDPR ELTN SEQ ID No. 7: Full length choriogenin L - Pacific salmon
MAMKWSVVCL VAVAMLGCLC VAQIWPPSIK PVQQPFRPNR
PPPQQPQQPP YQKPRIPPKD QTQAKQKFET PLDWTYPLDP
KPEPKIIGGS EARTPVAANS VRAECRENMV HVEAKHDLLG
IGQLIQLEDL TLGDCPMSGF DNINQVLIFE SPLQSCGSQL
RMTTNSLIYI FTLYYKPKPL ANTPLIRTND AMINIECHYP
RKHNVSSLAL IPTWTPFSAA KYAEELLYFS MRLMTADWQY
ERAGNMYVLG DMVNIEASVM QYFHVPLRIF VDSCVATLEP
NINANPRYAF IENHGCLIDA KMTGSHSQFM PRSADYKLYF
QVEAFRFQSQ RGSDPIIPQK TKIPFQPAAD YPATLDMIFL
TCHLKATTIA FPIDFEYKAC SFINTWREAG GNDGVCGCCD
STCSNRKGRD TTTHQKPANI WEGDVQLGPI FISEKVEQ SEQ ID No. 8: Alternative zr-protein - Atlantic salmon
KWSYQLPQKL AQPLPQKPAQ PLPQWPVQPL PQRPAEPLPQ
RPAQPLPQWP VQPLPQRPAE PLPQRPAQPL PQRPVQPLPQ
RPAQPFLQKP AQPIPQRIPY TKDDTKQTCE VVDKDKVSCG
LSGITAAQCQ AISCCFDGRM CFYGKTVTFQ CTKDGQFVVV
VSRDATLPNL ELDSISLLGA NGAHCTPVGT TSAFAIYQFK
VTECGTVVTE EPDTIVYENR MSSSYVVGIG PFGDITRDSH
YDLVFQCRYT GTSVETLVIE VKTYPNPNPV VTVDAVLNVE
LRLANGRCLS KGCDEMQEAY TSYYTVADYP VTKVLRDPVY
AEVRILGMTD PNVVLTLEQC WATTDPTGDR LPRWDLLVNG
CPYQDDRYLT VPIASDSSYI PPGEFLSHYK RFVFKMFTFV
DPTSMVPLQE NVYIHCRATV CHALAGSCEQ RCNRQRRDLS
AQGQKKTKGD VVVSSQKVIM IDPSLYA SEQ ID No. 9: leukolectin polypeptide from salmon embryo:
MRTTAAFLLVLCLLAISHAWDCQEVVNIKNLMQIDAGLGQVVATDTSQIP
YYLVGDKWIRLPGSLKHITVGPAGIWGVNKDYAIYKYVAGNWVQAAGLLK
QLDAGGEQFIVGANMNDTPYCLTSSATVGYKGPGSPLPWTGLPGAVKYYS
CGPFGCWAVNKNDDIYLMSLNQDCQNKGWSHIEGKLSMIEVATDGSVFGV
NSAGSVYTRDGITASKPEGTGWSNIPMGMLMGHVTYDLGRLWVVSKSAVT
MVCTH SEQ ID No. 10: leukolectin polypeptide from salmon leukocytes:
SIPYYLVGDKWIRLPGSLKHITVGPAGIWGVNKDYAIYKYVAGNWVQAAG
LPKQLDAGGEQFIVGANMDDTPYCLTSSATVGYKGPGSPLPWTGLPGAVK
YYSCGPFGCWAVNKNDDIYLMSLNQDCQNNGWSHIEGKLSMIEVATDGSV
FGVNSAGSVYTRDGITASKPEGTGWSNIPMCMLMGHVTYDLGRLWVVSKS
AVTMVCTH SEQ ID No. 11: leukolectin-2 polypeptide from salmon:
MRTTAAFLLVLCLLAISHAWDCQEVVNIKNLMQIDAGLGQVVATDTSQIP
YYLVGDKWIRLPGSLKHITVGPAGIWGVNKDYAIYKYVAGNWVQAAGLLK
QLDAGGNQFVVGANMDDTPFCLTSSATVGYKGPGSPLPWTGLPGAVKYYS
CGHFGCWAVNKNDDIFLMSLNQDCQNNGWSHIDGKLSMIEVATDGSVFGV
NSAGSVYTRDGITASKPEGTGWSNIPMGMLMGHVTYDLGRLWVVSKSGGT
MVCTH SEQ ID No. 12: leukolectin-3 polypeptide from salmon:
MGTTAAFLLVLCLLAISHAWDCQEVVNIKNLMQIDAGLGQVVATDTSQIP
YYLVGDKWIRLPGSLKHITVGPAGIWGVNKDYAIYKYVAGNWVQAAGLLK
QLDAGGEQFIVGANMNDTPYCLTSSATVGYKGPGSPLPWTGLPGAVKYYS
CGPFGCWAVNKNDDIYLMSLNQDCQNKGWSHIEGKLSMIEVATDGSVFGV
NSAGSVYTRDGITASKPEGTGWSNIPMGMLMGHVTYDLGRLWVVYKSAVT
MVCTH

The invention claimed is:

1. A method of preparing a pharmaceutical or cosmetic composition from fish hatching fluid comprising at least the steps of:
   a) suspending fish eggs in a minimal volume of water;
   b) inducing synchronized, rapid hatching of said eggs;
   c) optionally filtering the hatched eggs to obtain hatching fluid; and
   d) filtering the hatching fluid of b) or c) to obtain a composition, wherein the step of filtering the hatching fluid comprises at least the steps of:
      (i) filtering the hatching fluid using a filter with a pore size of at least 5 μm and collecting the filtrate;
      (ii) subjecting the filtrate from step (i) to ion exchange chromatography comprising:
         (1) loading the filtrate on to a DEAE (diethylaminoethyl) ion exchange column;
         (2) washing the column with a buffered wash solution at a pH of 7-9;
         (3) eluting leukolectin polypeptides from the column using a first elution buffer comprising the buffered wash solution further comprising a salt at a concentration of 50-100 mM;
         (4) eluting the remaining polypeptides from the column using a second elution buffer comprising the buffered wash solution comprising a salt at a concentration of 500 mM to 2M;
         (5) collecting the eluate from step (4);
   e) exchanging the water in the eluate from step (5) with a pharmaceutically or cosmetically acceptable buffer by performing diafiltration using a filter with an exclusion size of less than 12 kDa;
   f) filtering the solution obtained from step (e) using a filter with a pore size of 0.15-0.30 μm and collecting the filtrate; and
   g) preparing said pharmaceutical or cosmetic composition from the filtrate from step (f).

2. The method of claim 1, comprising an additional step of filtering the filtrate from step (i) using a filter with a pore size of 0.30-0.60 μm and collecting the filtrate.

3. The method of claim 1, wherein:
   a) the pore size of the filter in step (i) is 5-15 μm;
   b) the pore size of the filter in claim 2 is 0.35-0.55 μm; and/or
   c) the pore size of the filter in step (f) is 0.22 μm.

4. The method of claim 1, wherein the eggs are from a fish selected from a fish of any Superorder selected from the list consisting of Osteoglossomorpha, Elopomorpha, Clupeomorpha, Ostariophysi, Protacanthopterygii, Stenopterygii, Cyclosquamata, Scopelomorpha, Lampridiomorpha, Polymyxiomorpha, Paracanthopterygii and Acanthopterygii.

5. The method of claim 4, wherein the fish is from any Order selected from the list consisting of Osteoglossiformes, Hiodontiformes, Elopiformes, Albuliformes, Notacanthiformes, Anguilliformes, Saccopharyngiformes, Clupeiformes, Gonorynchiformes, Cypriniformes, Characiformes, Gymnotiformes, Siluriformes, Argentiniformes, Salmoniformes, Esociformes, Osmeriformes, Ateleopodiformes, Stomiiformes, Aulopiformes, Myctophiformes, Lampriformes, Polymixiiformes, Percopsiformes, Batrachoidiformes, Lophiiformes, Gadiformes, Ophidiiformes, Mugiliformes, Atheriniformes, Beloniformes, Cetomimiformes, Cyprinodontiformes, Stephanoberyciformes, Beryciformes, Zeiformes, Gobiesociformes, Gasterosteiformes, Syngnathiformes, Synbranchiformes, Tetraodontiformes, Pleuronectiformes, Scorpaeniformes Perciformes and Acipenseriformes.

6. The method of claim 5, wherein the fish is from any Family selected from the list consisting of Salmonidae, Cyprinidae, Cichlidae, Pangasiidae, Sciaenidae, Serranidae, Carangidae, Sparidae, Lateolabracidae, Moronidae, Mugilidae, Latidae, Eleotridae and Acipenseridae.

7. The method of claim 6, wherein the fish is a species selected from the list consisting of Grass carp (*Ctenopharyngodon idella*), Silver carp (*Hypophthalmichthys molitrix*), Catla (*Catla catla*), Common carp (*Cyprinus carpio*), Bighead carp (*Hypophthalmichthys nobilis*), Crucian carp (*Carassius carassius*), Nile tilapia (*Oreochromis niloticus niloticus*), Pangas catfish (*Pangasius pangasius*), Roho labeo (*Labeo rohita*), Atlantic salmon (*Salmo salar*), Large yellow croaker (*Larimichthys crocea*), Greasy grouper (*Epi-

*nephelus tauvina*), Sea trout (*Salmo trutta trutta*), Japanese amberjack (*Seriola quinqueradiata*), Gilthead seabream (*Sparus aurata*), Japanese seabass (*Lateolabrax japonicus*), European seabass (*Dicentrarchus labrax*), Silver seabream (*Chrysophrys auratus*), Flathead grey mullet (*Mugil cephalus*), Barramundi (*Lates calcarifer*), Marble goby (*Oxyeleotris marmorata*), Mozambique tilapia (*Oreochromis mossambicus*), Salmon trout (*Oncorhynchus mykiss*), Coho salmon (*Oncorhynchus kisutch*), Chinook salmon (*Oncorhynchus tshawytscha*), Pink salmon (*Oncorhynchus gorbuscha*), Chum salmon (*Oncorhynchus keta*), Sockeye salmon (*Oncorhynchus nerka*), Siberian sturgeon (*Acipenser baerii*) and Danube sturgeon (*Acipenser gueldenstaedtii*).

8. The method as claimed in claim 1, wherein hatching is complete within less than 2 hours for more than 95% of the embryos.

9. The method of claim 1 further comprising a step of coating or impregnating a product, material or device with the pharmaceutical or cosmetic composition of step (g) or chemically bonding the pharmaceutical or cosmetic composition of step (g) to a product, material or device.

10. The method of claim 1, wherein hatching is complete within less than 6 hours for more than 80% of the embryos.

11. The method of claim 1, wherein the pore size of the filter in step (i) is 7 μm.

12. The method of claim 2, wherein the additional step of filtering the filtrate from step (i) uses a filter with a pore size of 0.45 μm.

* * * * *